(12) United States Patent
Sawai et al.

(10) Patent No.: US 8,822,195 B2
(45) Date of Patent: Sep. 2, 2014

(54) POLYPEPTIDE HAVING D-LACTATE DEHYDROGENASE ACTIVITY, POLYNUCLEOTIDE ENCODING THE POLYPEPTIDE, AND PROCESS FOR PRODUCTION OF D-LACTIC ACID

(75) Inventors: Kenji Sawai, Kamakura (JP); Kazumi Suda, Kamakura (JP); Hideki Sawai, Kamakura (JP); Katsushige Yamada, Kamakura (JP); Junya Yamagishi, Kamakura (JP)

(73) Assignee: Toray Industries, Inc. (JP)

( * ) Notice: Subject to any disclaimer, the term of this patent is extended or adjusted under 35 U.S.C. 154(b) by 0 days.

(21) Appl. No.: 13/375,882

(22) PCT Filed: Jun. 2, 2010

(86) PCT No.: PCT/JP2010/059306
§ 371 (c)(1),
(2), (4) Date: Dec. 7, 2011

(87) PCT Pub. No.: WO2010/140602
PCT Pub. Date: Dec. 9, 2010

(65) Prior Publication Data
US 2012/0070871 A1    Mar. 22, 2012

(30) Foreign Application Priority Data
Jun. 3, 2009 (JP) ................. 2009-134213

(51) Int. Cl.
*C12N 1/20* (2006.01)
*C12N 15/00* (2006.01)
*C12N 9/04* (2006.01)
*C12P 7/56* (2006.01)

(52) U.S. Cl.
CPC .............. *C12P 7/56* (2013.01); *C12N 9/0006* (2013.01)
USPC ............... 435/252.3; 435/320.1; 435/254.2; 435/190

(58) Field of Classification Search
CPC ........................................ C12N 15/81
USPC ................................ 435/139, 190, 254.2
See application file for complete search history.

(56) References Cited

U.S. PATENT DOCUMENTS

| | | | |
|---|---|---|---|
| 4,719,246 A | 1/1988 | Murdoch et al. | |
| 8,071,357 B2* | 12/2011 | Sawai et al. | 435/254.2 |

FOREIGN PATENT DOCUMENTS

| | | |
|---|---|---|
| JP | S61-36321 | 2/1986 |
| JP | S63-241024 | 10/1988 |
| JP | 2000-17163 | 1/2000 |
| JP | 2006-280368 | 10/2006 |
| JP | 2007-074939 | 3/2007 |
| JP | 2008-029329 | 2/2008 |
| JP | 2008-048726 | 3/2008 |
| WO | 2004/104202 | 12/2004 |
| WO | 2007/043253 | 4/2007 |
| WO | 2007/097260 | 8/2007 |
| WO | 2009/004922 | 1/2009 |
| WO | 2009/072593 | 6/2009 |

OTHER PUBLICATIONS

ID Q9BLF6_OCTVU AC Q9BLF6; DT Jun. 1, 2001 (Embedded in Office Action).*
Witkowski et al., Biochemistry. Conversion of a â-Ketoacyl Synthase to a Malonyl Decarboxylase by Replacement of the Active-Site Cysteine with Glutamine 38:11643-11650, 1999.*
Broun et al., Science. Catalytic Plasticity of Fatty Acid Modification Enzymes Underlying Chemical Diversity of Plant Lipids 282:1315-1317, 1998.*
Devos et al., Proteins: Structure, Function and Genetics. Practical Limits of Function Prediction. 2000, vol. 41: 98-107.*
Database UniProt, "SubName: Full=Glyoxylate/hydroxypyruvate reductase, putative; EC=1.1.1.26," (online) Feb. 10, 2009, XP-002683909, retrieved from EBI accession No. UNIPORT:B7PV15, Database accession No. B7PV15, 1 sheet.
Selander, R.K. et al., "Horseshoe-Crab Lactate Dehydrogenases Evidence for Dimeric Structure," *Science* (Washington D.C.), vol. 169, No. 3941, 1970, pp. 179-181, XP007921065, ISSN: 0036-8075.
Massaro, E. J.: "Horseshoe-Crab Lactate Dehydrogenase Tissue Distribution and Molecular Weight," *Science* (Washington D.C.), vol. 167, No. 3920, 1970, pp. 994-996, XP007921067, ISSN: 0036-8075.
Database EMBL, "*Limulus polyphemus* EST, 5'-end sequence, clone dmp036cmP0008G13," (online) Jan. 7, 2010, XP-002683910, retrieved from EBI accession No. EM_EST:FN230952 Database accession No. FN230952, 1 sheet.
Long, G.L. at al., "Diphosphopyridine Nucleotide-linked D-lactate Dehydrongenases from the Horseshoe Crab, *Limulus polyphemus* and the Seaworm *Nereis virens*. I. Physical and Chemical Properties," *Arch. Biochem. Biophys*. 1973, vol. 154, pp. 696-710.
Long, G.L. at al., "Diphosphopyridine Nucleotide-linked D-lactate Dehydrongenases from the Horseshoe Crab, *Limulus polyphemus* and the Seaworm, *Nereis virens*. II. Catalytic Properties," *Arch Biochem. Biophys*, 1973, vol. 154, pp. 711-725.

(Continued)

*Primary Examiner* — Tekchand Saidha
*Assistant Examiner* — Rama P Ramanujam
(74) *Attorney, Agent, or Firm* — DLA Piper LLP (US)

(57) ABSTRACT

Highly productive D-lactic acid fermentation uses a transformant obtained by introducing into a host cell a polynucleotide encoding a polypeptide according to any one of the following (A) to (C) in such a manner that the polypeptide is expressed, which polypeptide has a D-lactate dehydrogenase activity higher than those of conventional polypeptides: (A) a polypeptide having the amino acid sequence shown in SEQ ID NO:1 or 2; (B) a polypeptide having the same amino acid sequence as shown in SEQ ID NO:1 or 2 except that one or several amino acids are substituted, deleted, inserted and/or added, which polypeptide has a D-lactate dehydrogenase activity; and (C) a polypeptide having an amino acid sequence which has a sequence identity of not less than 80% to the amino acid sequence shown in SEQ ID NO:1 or 2, which polypeptide has a D-lactate dehydrogenase activity.

14 Claims, 2 Drawing Sheets

(56) References Cited

OTHER PUBLICATIONS

Long, G.L "D-Lactate Dehydrogenase from the Horseshoe Crab," *Methods. Enzymol.*, 1975, vol. 41, pp. 313-318.

Siebenaller J.F, et al., "Comparison of the D-lactate Stereospecific Dehydrogenases of *Limulus polyphemus* with Active-site Regions of L-lactate Dehydrogenases," *Biochim. Biophys. Acta.*, 1983, vol. 749. No, 2, pp. 153-162.

Gerl, M. et al., "Mechanism and Specificity of Reconstitution of Dimeric Lactate Dehydrogenase from *Limulus polyphemus*," *Biol. Chem. Hoppe Seyler*, May 1985, vol. 366, No. 5, pp. 447-454.

Siebenaller JF et al., "Comparison of the D-lactate stereospecific dehydrogenase of *Limulus polyphemus* with active-site regions of L-lactate dehydrogenases," *Biochim. Biophys. Acta.* Dec. 12, 1983;vol. 749, No. 2, pp. 153-162. Abstract only.

Gerl, M., "Mechanism and specificity of reconstitution of dimeric lactate dehydrogenase from *Limulus polyphemus*," *Biol. Chem. Hoppe Seyler*, May 1985; vol. 366, No. 5, pp. 447-454. Abstract only.

Tuengler, P. et al., "Studies on the active center of D- and L-lactate dehydrogenases using oxamate-diaminohexyl-Sepharose affinity Chromatography," *Proc. Natl. Acad. Sci. USA*, Oct. 1980; vol. 77, No. 10, pp. 5832-5836.

Long, G.L. et al. "Affinity chromatography of d-lactate dehydrogenases from *Limulus polyphemus* (horseshoe crab) and Haliotus sp. (abalone) voluntary muscle on 8-(6-aminohexyl)-amino-adenine nucleotide-sepharose," *J Solid-Phase Biochem.*, 1976, vol. 1, No. 4, pp. 307-317.

Long, G.L. et al., "Diphosphopyridine nucleotide-linked D-lactate dehydrogenases from the horseshoe crab, *Limulus polyphemus*, and the seaworm, *Nereis virens*. II. Catalytic properties," *Arch. Biochem. Biophys.*, 1973, vol. 154, pp. 711-725. Abstract Only.

Ishida, N. et al. "D-lactic acid production by metabolically engineered *Saccharomyces cerevisiae*," *J Biosci Bioeng.*, Feb. 2006, vol. 101, No. 2, pp. 172-1777.

Garmyn, D. et al., "Cloning, Nucleotide Sequence, and Transcriptional Analysis of the *Pediococcus acidilactici* L-(+)-Lactate Dehydrogenase Gene," *Appl. Environ. Micribiol.*, Jan. 1995, vol. 61, No. 1, pp. 266-272.

\* cited by examiner

SEQUENCE LISTING

<160> NUMBER OF SEQ ID NOS: 60

<210> SEQ ID NO 1
<211> LENGTH: 326
<212> TYPE: PRT
<213> ORGANISM: Limulus polyphemus

<400> SEQUENCE: 1

Met Ser Lys Pro Lys Val Phe Val Thr Arg Pro Asp Val Pro Gln Ala
1               5                   10                  15

Gly Ile Asp Leu Leu Lys Glu Lys Cys Asp Val Glu Ile Tyr Asp Gln
            20                  25                  30

Pro Met Pro Ile Pro Arg Asp Ala Leu Ile Lys Gly Val Gln Gly Lys
        35                  40                  45

Asp Ala Leu Tyr Cys Leu Leu Thr Asp Lys Ile Asp Lys Asp Val Met
    50                  55                  60

Asp Ala Ala Gly Pro Gln Leu Lys Val Ile Ala Thr Met Ser Val Gly
65                  70                  75                  80

Phe Asp His Ile Asp Leu Asn Glu Cys Lys Ala Arg Asn Ile Ala Val
                85                  90                  95

Ser Asn Thr Pro Asp Val Ser Thr Asp Ser Val Ala Glu Leu Thr Val
            100                 105                 110

Thr Leu Leu Leu Val Cys Gly Arg Arg Ile Met Asp Ser Ala Asn Ala
        115                 120                 125

Ile Lys Asn Gly Glu Trp Ile Tyr Ser Trp Ser Pro Leu Trp Leu Cys
130                 135                 140

Gly Arg Gly Leu Thr Asn Ser Thr Ile Gly Ile Val Gly Met Gly Arg
145                 150                 155                 160

Ile Gly Gln Ala Val Met Lys Arg Leu Leu Pro Phe Gly Val Lys Lys
                165                 170                 175

Val Leu Tyr Tyr Asp Leu Phe His Pro Ile Lys Pro Ala Glu Asp Met
            180                 185                 190

Gly Ala Gln Tyr Val Glu Phe Glu Glu Leu Leu Lys Glu Ser Asp Phe
        195                 200                 205

Val Val Ala Met Cys Asn Leu Ser Glu Gln Thr Lys Glu Leu Phe Asn
    210                 215                 220

Ala Lys Ala Phe Ser Gln Met Lys Pro Thr Ala Val Phe Val Asn Thr
225                 230                 235                 240

Ser Arg Gly Gly Val Val Gln Gln Asp Leu Tyr Glu Ala Leu Lys
                245                 250                 255

Asn Gly Lys Ile Arg Ala Ala Gly Leu Asp Val Met Ile Pro Glu Pro
            260                 265                 270

Leu Pro Arg Asp His Lys Leu Thr Thr Leu Pro Asn Ile Val Leu Leu
        275                 280                 285

Pro His Val Gly Ser Ala Glu Glu Ala Ala Arg Ile Glu Met Ala Thr
    290                 295                 300

Leu Ala Ala Lys Asn Ile Leu Ser Val Leu Asp Gly Lys Pro Leu Val
305                 310                 315                 320

Thr Pro Val Pro Met Pro
                325

<210> SEQ ID NO 2
<211> LENGTH: 326
<212> TYPE: PRT
<213> ORGANISM: Limulus polyphemus

<400> SEQUENCE: 2

Met Ser Lys Pro Lys Val Phe Val Thr Arg Pro Asp Val Pro Gln Ala
1               5                   10                  15

Gly Ile Asp Leu Leu Lys Glu Lys Cys Asp Val Glu Ile Tyr Asp Gln
            20                  25                  30

Pro Met Pro Ile Pro His Asp Ala Leu Ile Lys Gly Val Gln Gly Lys
        35                  40                  45

Asp Ala Leu Tyr Cys Leu Leu Thr Asp Lys Ile Asp Lys Asp Val Met
    50                  55                  60

Asp Ala Ala Gly Pro Gln Leu Lys Val Ile Ala Thr Met Ser Val Gly
65                  70                  75                  80

Tyr Asp His Ile Asp Leu Asn Glu Cys Lys Ala Arg Asn Ile Val Val
                85                  90                  95

Ser Asn Thr Pro Asp Val Ser Thr Asp Ser Val Ala Glu Leu Thr Val
            100                 105                 110

Thr Leu Leu Leu Val Val Gly Arg Arg Ile Phe Asp Ser Ala Cys Ala
        115                 120                 125

Ile Lys Asn Gly Glu Trp Ile Tyr Ser Trp Ser Pro Leu Trp Leu Cys
    130                 135                 140

Gly Arg Gly Leu Thr Asn Ser Thr Val Gly Ile Val Gly Met Gly Arg
145                 150                 155                 160

Ile Gly Gln Ala Val Met Lys Arg Leu Leu Pro Phe Gly Val Lys Lys
                165                 170                 175

Ile Leu Tyr Phe Asp Leu Phe His Pro Ile Lys Pro Ala Glu Asp Met
            180                 185                 190

Gly Ala Gln Phe Val Glu Phe Glu Glu Leu Leu Lys Glu Ser Asp Phe
        195                 200                 205

Val Val Ala Met Cys Asn Leu Ser Glu Glu Thr Lys Glu Ile Phe Asn
    210                 215                 220

Ala Lys Ala Phe Ser Leu Met Lys Pro Thr Ala Val Phe Ile Asn Thr
225                 230                 235                 240

Ser Arg Gly Gly Val Val Gln Gln Asp Asp Leu Tyr Glu Ala Leu Lys
                245                 250                 255

Asn Gly Val Ile Arg Gly Ala Gly Leu Asp Val Met Val Pro Glu Pro
            260                 265                 270

Leu Pro Arg Asp His Lys Leu Thr Thr Leu Pro Asn Ile Ile Leu Leu
        275                 280                 285

Pro His Val Gly Ser Ala Glu Glu Ala Ala Arg Thr Glu Met Ala Thr
    290                 295                 300

Leu Ala Ala Lys Asn Ile Leu Ser Val Leu Asp Gly Lys Pro Leu Leu
305                 310                 315                 320

Thr Pro Val Gln Met Pro
                325

<210> SEQ ID NO 3
<211> LENGTH: 981
<212> TYPE: DNA
<213> ORGANISM: Limulus polyphemus

<400> SEQUENCE: 3
atgagcaaac caaaggtatt tgtaaccaga ccagacgttc ctcaagcagg aattgacctt      60
ttaaaggaaa aatgtgatgt agaaatttac gaccagccga tgccgattcc acgagatgcc     120
ttaattaaag gagttcaggg taaggatgct ctttattgtc ttctcacgga caaaattgac     180

| | |
|---|---|
| aaggatgtga tggatgcagc aggaccccag ctaaaggtaa tagcgaccat gtctgttgga | 240 |
| tttgaccata ttgaccttaa cgaatgtaag gcaagaaata ttgcggtcag caacactccc | 300 |
| gatgtttcca ctgactccgt agctgagctg actgtcacac tattgttggt ttgtggcaga | 360 |
| agaatcatgg attctgcaaa cgctattaaa aatggagagt ggatctactc ttggagtcca | 420 |
| ctgtggctat gtggtagagg attaaccaac agcacaatag gaattgtagg aatgggtaga | 480 |
| attggccaag ctgtcatgaa acgcctgttg cctttcggtg taagaaggt tttgtattat | 540 |
| gatctatttc acccaatcaa acccgctgaa gacatgggag ctcagtatgt tgagtttgaa | 600 |
| gagttattga agagtcaga cttttgtagtc gcaatgtgca atttatcaga acaaaccaag | 660 |
| gaattgttta atgccaaggc tttcagccaa atgaagccta cagcagtttt cgttaatact | 720 |
| agtcgcggag gagttgttca acaagatgac ctctatgagg ccctcaagaa tggcaagatc | 780 |
| cgtgctgcag gcttgacgt aatgattcct gagcctctac cccgggatca caagcttact | 840 |
| actttaccaa acatagttct tcttccacat gttggcagtg ctgaggaagc agcaagaata | 900 |
| gaaatggcaa ccttggcagc taagaacatc ttgtccgttt tagatggaaa gcctcttgta | 960 |
| actcctgttc ccatgccata a | 981 |

<210> SEQ ID NO 4
<211> LENGTH: 981
<212> TYPE: DNA
<213> ORGANISM: Limulus polyphemus

<400> SEQUENCE: 4

| | |
|---|---|
| atgagcaagc ccaaagtatt tgtcactaga cctgatgttc ctcaggcagg aattgatctt | 60 |
| ttgaaagaga atgcgatgt cgaaatctat gatcagccta tgccaattcc acatgatgct | 120 |
| cttattaaag gagtgcaggg taaggacgct ctttattgtc tcctcaccga taagattgat | 180 |
| aaagatgtta tggatgcagc tgggcctcag ctaaaagtta tagctaccat gtctgttgga | 240 |
| tatgaccata ttgaccttaa tgaatgtaag gcaagaaata tagttgtaag taacactcct | 300 |
| gacgtatcca ctgactcagt agcagaactt actgttacac ttttattggt tgttggtaga | 360 |
| agaatttttg attctgcctg tgccattaaa aatggagagt ggatttactc atggagtcct | 420 |
| ttgtggttgt gtggtcgagg attgaccaac agcaccgtag gaattgttgg tatgggaaga | 480 |
| attggtcaag cagtcatgaa gagacttcta ccgtttggag ttaagaaaat tttatacttt | 540 |
| gacctgtttc atccaatcaa gcctgcagaa gatatgggag ctcagtttgt tgaatttgaa | 600 |
| gagctgttga agaatctga tttgtagtt gccatgtgta atctgtctga ggaaacaaag | 660 |
| gagatattta acgccaaggc tttcagtcta atgaagccta ctgcagtttt tataaatacc | 720 |
| agccgtggtg gagttgtgca gcaggatgac ttgtatgaag cccttaagaa tggcgtgatc | 780 |
| cgtggggccg gactggacgt gatggttcct gagcctttac cccgggacca caaactcaca | 840 |
| acactaccaa acataattct tctcccgcat gttggcagtg ctgaggaagc agcaagaaca | 900 |
| gaaatggcaa ctctggcagc caaaaacatc ctttccgttt tagatgggaa gccacttttg | 960 |
| actccagttc aaatgccata a | 981 |

<210> SEQ ID NO 5
<211> LENGTH: 1000
<212> TYPE: DNA
<213> ORGANISM: Saccharomyces cerevisiae

<400> SEQUENCE: 5

| | |
|---|---|
| aaaatgaagg ccaaatcaag gcgggaaggg acaaccagga cgtaaagggt agcctcccca | 60 |

```
taacataaac tcaataaaat atatagtctt caacttgaaa aaggaacaag ctcatgcaaa      120
gaggtggtac ccgcacgccg aaatgcatgc aagtaaccta ttcaaagtaa tatctcatac      180
atgtttcatg agggtaacaa catgcgactg ggtgagcata tgttccgctg atgtgatgtg      240
caagataaac aagcaaggca gaaactaact tcttcttcat gtaataaaca cacccgcgt       300 ttatttacct atctctaaac ttcaacacct tatatcataa ctaatatttc ttgagataag      360
cacactgcac ccatacccttc cttaaaaacg tagcttccag tttttggtgg ttccggcttc     420
cttcccgatt ccgcccgcta aacgcatatt tttgttgcct ggtggcattt gcaaaatgca     480
taacctatgc atttaaaaga ttatgtatgc tcttctgact tttcgtgtga tgaggctcgt      540
ggaaaaaatg aataatttat gaatttgaga acaattttgt gttgttacgg tatttactg       600 tggaataatc aatcaattga ggattttatg caaatatcgt ttgaatatt tccgacccct       660 ttgagtactt ttcttcataa ttgcataata ttgtccgctg ccccttttc tgttagacgg       720 tgtcttgatc tacttgctat cgttcaacac caccttattt tctaactatt ttttttttag      780
ctcatttgaa tcagcttatg gtgatggcac atttttgcat aaacctagct gtcctcgttg      840
aacataggaa aaaaaatat ataaacaagg ctctttcact ctccttgcaa tcagatttgg      900
gtttgttccc tttattttca tatttcttgt catattcctt tctcaattat tattttctac      960
tcataacctc acgcaaaata acacagtcaa atcaatcaaa                           1000

<210> SEQ ID NO 6
<211> LENGTH: 1000
<212> TYPE: DNA
<213> ORGANISM: Saccharomyces cerevisiae

<400> SEQUENCE: 6 aggatttttaa tctgttggag ttaaggtgaa tacgttttc catattgggg tatgcagctc       60
gaacctaaag tggtatgtac acatcccctc aagcacaccc attacccttaa taggattaat     120 gtaagcaaca gcttacacgg aattggaaat actattcaac gatccatgca tctgccagat      180
tcggacatgc atattcccca attggatata gaaaattaac gtaaggcagt atcttttcac     240
aatgtacttg caacgcggcg acttaaagtt gaagtacaac ctgcagcagc ggcttttttgt    300 acggtacgcc aaactgtcaa tggataatat tgcgtagacc gaaaaaggta atcctcaaca     360
ctacccgtgg tggatgacct aaagcagtaa tattggttgg aattatctcc cagacggcac     420
cgtctccccg agaaagctta gccccgaggt ctaccttcca tacaccactg attgctccac     480
gtcatgcggc cttctttcga ggacaaaaag gcatatatcg ctaaaattag ccatcagaac     540
cgttattgtt attatatttt cattacgaaa gaggagaggg cccagcgcgc cagagcacac     600
acggtcattg attactttat ttggctaaag atccatccct tctcgatgtc atctctttcc     660
attcttgtgt attttttgatt gaaaatgatt ttttgtccac taatttctaa aaataagaca    720
aaaagccttt aagcagtttt tcatccattt tactacggta aaatgaatta gtacggtatg    780
gctcccagtc gcattattt tagattggcc gtaggggctg gggtagaact agagtaagga      840
acattgctct gccctctttt gaactgtcat ataaatacct gacctatttt attctccatt     900
atcgtattat ctcacctctc ttttctatt ctcttgtaat tattgattta tagtcgtaac      960
tacaaagaca agcaaaataa aatacgttcg ctctattaag                           1000

<210> SEQ ID NO 7
<211> LENGTH: 1000
<212> TYPE: DNA
```

<213> ORGANISM: Saccharomyces cerevisiae

<400> SEQUENCE: 7

```
ctattttcga ggaccttgtc accttgagcc caagagagcc aagatttaaa ttttcctatg    60
acttgatgca aattcccaaa gctaataaca tgcaagacac gtacggtcaa gaagacatat   120
ttgacctctt aacaggttca gacgcgactg cctcatcagt aagacccgtt gaaaagaact   180
tacctgaaaa aaacgaatat atactagcgt tgaatgttag cgtcaacaac aagaagttta   240
atgacgcgga ggccaaggca aaaagattcc ttgattacgt aagggagtta gaatcatttt   300
gaataaaaaa cacgcttttt cagttcgagt ttatcattat caatactgcc atttcaaaga   360
atacgtaaat aattaatagt agtgattttc ctaactttat ttagtcaaaa aattagcctt   420
ttaattctgc tgtaacccgt acatgcccaa ataggggc gggttacaca gaatatataa    480
catcgtaggt gtctgggtga acagtttatt cctggcatcc actaaatata atggagcccg   540
ctttttaagc tggcatccag aaaaaaaaag aatcccagca ccaaatatt gttttcttca    600
ccaaccatca gttcataggt ccattctctt agcgcaacta cagagaacag gggcacaaac   660
aggcaaaaaa cgggcacaac ctcaatggag tgatgcaacc tgcctggagt aaatgatgac   720
acaaggcaat tgacccacgc atgtatctat ctcattttct tacaccttct attaccttct   780
gctctctctg atttggaaaa agctgaaaaa aaaggttgaa accagttccc tgaaattatt   840
cccctacttg actaataagt atataaagac ggtaggtatt gattgtaatt ctgtaaatct   900
atttcttaaa cttcttaaat tctacttta tagttagtct ttttttagt tttaaaacac     960
caagaactta gtttcgaata acacacata  aacaaacaaa                        1000
```

<210> SEQ ID NO 8
<211> LENGTH: 20
<212> TYPE: DNA
<213> ORGANISM: Artificial
<220> FEATURE:
<223> OTHER INFORMATION: primer

<400> SEQUENCE: 8

```
atcdchacya tstcbgtggg                                                20
```

<210> SEQ ID NO 9
<211> LENGTH: 17
<212> TYPE: DNA
<213> ORGANISM: Artificial
<220> FEATURE:
<223> OTHER INFORMATION: primer

<400> SEQUENCE: 9

```
ggytcdggva ccatyac                                                   17
```

<210> SEQ ID NO 10
<211> LENGTH: 27
<212> TYPE: DNA
<213> ORGANISM: Artificial
<220> FEATURE:
<223> OTHER INFORMATION: primer

<400> SEQUENCE: 10

```
ttgccattct tgagggcctc atagagg                                        27
```

<210> SEQ ID NO 11
<211> LENGTH: 24
<212> TYPE: DNA
<213> ORGANISM: Artificial

```
-continued

<220> FEATURE:
<223> OTHER INFORMATION: primer

<400> SEQUENCE: 11
gctgcacaac tccaccacgg ctgg                                              24

<210> SEQ ID NO 12
<211> LENGTH: 24
<212> TYPE: DNA
<213> ORGANISM: Artificial
<220> FEATURE:
<223> OTHER INFORMATION: primer

<400> SEQUENCE: 12
tcagctcagc tacggagtca gtgg                                              24

<210> SEQ ID NO 13
<211> LENGTH: 24
<212> TYPE: DNA
<213> ORGANISM: Artificial
<220> FEATURE:
<223> OTHER INFORMATION: primer

<400> SEQUENCE: 13
actattgttg gtttgtggca gaag                                              24

<210> SEQ ID NO 14
<211> LENGTH: 24
<212> TYPE: DNA
<213> ORGANISM: Artificial
<220> FEATURE:
<223> OTHER INFORMATION: primer

<400> SEQUENCE: 14
taagttctgc tactgagtca gtgg                                              24

<210> SEQ ID NO 15
<211> LENGTH: 24
<212> TYPE: DNA
<213> ORGANISM: Artificial
<220> FEATURE:
<223> OTHER INFORMATION: primer

<400> SEQUENCE: 15
tagaagaatt tttgattctg cctg                                              24

<210> SEQ ID NO 16
<211> LENGTH: 24
<212> TYPE: DNA
<213> ORGANISM: Artificial
<220> FEATURE:
<223> OTHER INFORMATION: primer

<400> SEQUENCE: 16
aacatcggga gtgttgctga ccgc                                              24

<210> SEQ ID NO 17
<211> LENGTH: 26
<212> TYPE: DNA
<213> ORGANISM: Artificial
<220> FEATURE:
<223> OTHER INFORMATION: primer

<400> SEQUENCE: 17
agagtggatc tactcttgga gtccac                                            26
```

```
<210> SEQ ID NO 18
<211> LENGTH: 24
<212> TYPE: DNA
<213> ORGANISM: Artificial
<220> FEATURE:
<223> OTHER INFORMATION: primer

<400> SEQUENCE: 18
tacgtcagga gtgttactta caac                                              24

<210> SEQ ID NO 19
<211> LENGTH: 26
<212> TYPE: DNA
<213> ORGANISM: Artificial
<220> FEATURE:
<223> OTHER INFORMATION: primer

<400> SEQUENCE: 19
agagtggatc tactcttgga gtccac                                            26

<210> SEQ ID NO 20
<211> LENGTH: 30
<212> TYPE: DNA
<213> ORGANISM: Artificial
<220> FEATURE:
<223> OTHER INFORMATION: primer

<400> SEQUENCE: 20
atgcctcgag atgagcaaac caaaggtatt                                        30

<210> SEQ ID NO 21
<211> LENGTH: 30
<212> TYPE: DNA
<213> ORGANISM: Artificial
<220> FEATURE:
<223> OTHER INFORMATION: primer

<400> SEQUENCE: 21
atgcgcggcc gcttatggca tgggaacagg                                        30

<210> SEQ ID NO 22
<211> LENGTH: 30
<212> TYPE: DNA
<213> ORGANISM: Artificial
<220> FEATURE:
<223> OTHER INFORMATION: primer

<400> SEQUENCE: 22
atgcctcgag atgagcaagc ccaaagtatt                                        30

<210> SEQ ID NO 23
<211> LENGTH: 30
<212> TYPE: DNA
<213> ORGANISM: Artificial
<220> FEATURE:
<223> OTHER INFORMATION: primer

<400> SEQUENCE: 23
atgcgcggcc gcttatggca tttgaactgg                                        30

<210> SEQ ID NO 24
<211> LENGTH: 75
<212> TYPE: DNA
<213> ORGANISM: Artificial
<220> FEATURE:
<223> OTHER INFORMATION: primer
```

```
<400> SEQUENCE: 24
attattattt tctactcata acctcacgca aaataacaca gtcaaatcaa tcaaaatgag    60
caaaccaaag gtatt                                                    75

<210> SEQ ID NO 25
<211> LENGTH: 20
<212> TYPE: DNA
<213> ORGANISM: Artificial
<220> FEATURE:
<223> OTHER INFORMATION: primer

<400> SEQUENCE: 25
aggcgtatca cgaggcoctt                                               20

<210> SEQ ID NO 26
<211> LENGTH: 75
<212> TYPE: DNA
<213> ORGANISM: Artificial
<220> FEATURE:
<223> OTHER INFORMATION: primer

<400> SEQUENCE: 26
attattattt tctactcata acctcacgca aaataacaca gtcaaatcaa tcaaaatgag    60
caagcccaaa gtatt                                                    75

<210> SEQ ID NO 27
<211> LENGTH: 60
<212> TYPE: DNA
<213> ORGANISM: Artificial
<220> FEATURE:
<223> OTHER INFORMATION: primer

<400> SEQUENCE: 27
gaattaattc ttgaagacga aagggcctcg tgatacgcct agattgtact gagagtgcac    60

<210> SEQ ID NO 28
<211> LENGTH: 80
<212> TYPE: DNA
<213> ORGANISM: Artificial
<220> FEATURE:
<223> OTHER INFORMATION: primer

<400> SEQUENCE: 28 tattttttcgt tacataaaaa tgcttataaa actttaacta ataattagag attaaatcgc    60
ctgtgcggta tttcacaccg                                               80

<210> SEQ ID NO 29
<211> LENGTH: 24
<212> TYPE: DNA
<213> ORGANISM: Artificial
<220> FEATURE:
<223> OTHER INFORMATION: primer

<400> SEQUENCE: 29
gacaattctg gttaggtcca agag                                          24

<210> SEQ ID NO 30
<211> LENGTH: 24
<212> TYPE: DNA
<213> ORGANISM: Artificial
<220> FEATURE:
<223> OTHER INFORMATION: primer
```

```
<400> SEQUENCE: 30
ttaagctgct gcggagcttc cacg                                           24

<210> SEQ ID NO 31
<211> LENGTH: 29
<212> TYPE: DNA
<213> ORGANISM: Artificial
<220> FEATURE:
<223> OTHER INFORMATION: primer

<400> SEQUENCE: 31
ccctcgagat gaagattttt gcttacggc                                      29

<210> SEQ ID NO 32
<211> LENGTH: 31
<212> TYPE: DNA
<213> ORGANISM: Artificial
<220> FEATURE:
<223> OTHER INFORMATION: primer

<400> SEQUENCE: 32
ccgcggccgc ttaatattca acagcaatag c                                   31

<210> SEQ ID NO 33
<211> LENGTH: 85
<212> TYPE: DNA
<213> ORGANISM: Artificial
<220> FEATURE:
<223> OTHER INFORMATION: primer

<400> SEQUENCE: 33
tctcaattat tattttctac tcataacctc acgcaaaata acacagtcaa atcaatcaaa    60
atgaagattt ttgcttacgg cattc                                          85

<210> SEQ ID NO 34
<211> LENGTH: 22
<212> TYPE: DNA
<213> ORGANISM: Artificial
<220> FEATURE:
<223> OTHER INFORMATION: primer

<400> SEQUENCE: 34
atggattcta gaacagttgg ta                                             22

<210> SEQ ID NO 35
<211> LENGTH: 22
<212> TYPE: DNA
<213> ORGANISM: Artificial
<220> FEATURE:
<223> OTHER INFORMATION: primer

<400> SEQUENCE: 35
ttacttgttt tctagataag ct                                             22

<210> SEQ ID NO 36
<211> LENGTH: 75
<212> TYPE: DNA
<213> ORGANISM: Artificial
<220> FEATURE:
<223> OTHER INFORMATION: primer

<400> SEQUENCE: 36
ttagttttaa aacaccaaga acttagtttc gaataaacac acataaacaa acaaaatgag    60
caaaccaaag gtatt                                                     75
```

<210> SEQ ID NO 37
<211> LENGTH: 22
<212> TYPE: DNA
<213> ORGANISM: Artificial
<220> FEATURE:
<223> OTHER INFORMATION: primer

<400> SEQUENCE: 37
atgtctgccc ctaagaagat cg                                              22

<210> SEQ ID NO 38
<211> LENGTH: 24
<212> TYPE: DNA
<213> ORGANISM: Artificial
<220> FEATURE:
<223> OTHER INFORMATION: primer

<400> SEQUENCE: 38
ttaagcaagg attttcttaa cttc                                            24

<210> SEQ ID NO 39
<211> LENGTH: 75
<212> TYPE: DNA
<213> ORGANISM: Artificial
<220> FEATURE:
<223> OTHER INFORMATION: primer

<400> SEQUENCE: 39
atttatagtc gtaactacaa agacaagcaa aataaaatac gttcgctcta ttaagatgag     60
caaaccaaag gtatt                                                      75

<210> SEQ ID NO 40
<211> LENGTH: 68
<212> TYPE: DNA
<213> ORGANISM: Artificial
<220> FEATURE:
<223> OTHER INFORMATION: primer

<400> SEQUENCE: 40
actcgcgcgc aagatctaag cggccgctaa tggatccaat aatcgatgct gtctttcttc     60
ttcatggg                                                              68

<210> SEQ ID NO 41
<211> LENGTH: 37
<212> TYPE: DNA
<213> ORGANISM: Artificial
<220> FEATURE:
<223> OTHER INFORMATION: primer

<400> SEQUENCE: 41
actcgcgcgc aagatctgaa cttctccaac aggtagc                              37

<210> SEQ ID NO 42
<211> LENGTH: 99
<212> TYPE: DNA
<213> ORGANISM: Artificial
<220> FEATURE:
<223> OTHER INFORMATION: primer

<400> SEQUENCE: 42
cggccgccag ctgaagcttc gtacgctgca ggtcgacaac ccttaatata acttcgtata     60
atgtatgcta tacgaagtta tcctttgctg tgttctacc                            99

<210> SEQ ID NO 43
<211> LENGTH: 68
<212> TYPE: DNA
<213> ORGANISM: Artificial
<220> FEATURE:
<223> OTHER INFORMATION: primer

<400> SEQUENCE: 43
tcgatcagaa acttctcgac agacgtcgcg gtgagttcag gcttttcat ctttatccgc       60 cagtatgt                                                              68

<210> SEQ ID NO 44
<211> LENGTH: 50
<212> TYPE: DNA
<213> ORGANISM: Artificial
<220> FEATURE:
<223> OTHER INFORMATION: primer

<400> SEQUENCE: 44
atgaaaaagc ctgaactcac cgcgacgtct gtcgagaagt ttctgatcga                 50

<210> SEQ ID NO 45
<211> LENGTH: 69
<212> TYPE: DNA
<213> ORGANISM: Artificial
<220> FEATURE:
<223> OTHER INFORMATION: primer

<400> SEQUENCE: 45
catgaggatc ataatttata acgtaatccc ataaataaaa gtcatacaat ctattccttt       60
gccctcgga                                                             69

<210> SEQ ID NO 46
<211> LENGTH: 50
<212> TYPE: DNA
<213> ORGANISM: Artificial
<220> FEATURE:
<223> OTHER INFORMATION: primer

<400> SEQUENCE: 46
attgtatgac ttttatttat gggattacgt tataaattat gatcctcatg                 50

<210> SEQ ID NO 47
<211> LENGTH: 83
<212> TYPE: DNA
<213> ORGANISM: Artificial
<220> FEATURE:
<223> OTHER INFORMATION: primer

<400> SEQUENCE: 47
taggccacta gtggatctga tatcacctaa taacttcgta tagcatacat tatacgaagt       60
tattcattca tccctcacta tcg                                             83

<210> SEQ ID NO 48
<211> LENGTH: 20
<212> TYPE: DNA
<213> ORGANISM: Artificial
<220> FEATURE:
<223> OTHER INFORMATION: primer

<400> SEQUENCE: 48
ggccgccagc tgaagcttcg                                                 20

```
<210> SEQ ID NO 49
<211> LENGTH: 20
<212> TYPE: DNA
<213> ORGANISM: Artificial
<220> FEATURE:
<223> OTHER INFORMATION: primer

<400> SEQUENCE: 49
aggccactag tggatctgat                                               20

<210> SEQ ID NO 50
<211> LENGTH: 44
<212> TYPE: DNA
<213> ORGANISM: Artificial
<220> FEATURE:
<223> OTHER INFORMATION: primer

<400> SEQUENCE: 50
actcggatcc ctgcaagcta ctttgtaatt aaacaaataa cggg                    44

<210> SEQ ID NO 51
<211> LENGTH: 80
<212> TYPE: DNA
<213> ORGANISM: Artificial
<220> FEATURE:
<223> OTHER INFORMATION: primer

<400> SEQUENCE: 51
ggagactctt cacactgttg gcgtctatga ttcaagattg tcagtttcca tcgtggattg    60
gaatagatct ggtgaccttg                                               80

<210> SEQ ID NO 52
<211> LENGTH: 90
<212> TYPE: DNA
<213> ORGANISM: Artificial
<220> FEATURE:
<223> OTHER INFORMATION: primer

<400> SEQUENCE: 52
acaactattc caatccacga tggaaactga caatcttgaa tcatagacgc caacagtgtg    60
aagagtctcc agctgaagct tcgtacgctg                                    90

<210> SEQ ID NO 53
<211> LENGTH: 40
<212> TYPE: DNA
<213> ORGANISM: Artificial
<220> FEATURE:
<223> OTHER INFORMATION: primer

<400> SEQUENCE: 53
actcggccgg ccatcgatca ctagtggatc tgatatcacc                         40

<210> SEQ ID NO 54
<211> LENGTH: 38
<212> TYPE: DNA
<213> ORGANISM: Artificial
<220> FEATURE:
<223> OTHER INFORMATION: primer

<400> SEQUENCE: 54
actcgcggcc gctctagaca ccaactttga agataggg                           38

<210> SEQ ID NO 55
<211> LENGTH: 64
<212> TYPE: DNA
```

<210> SEQ ID NO 56
<211> LENGTH: 64
<212> TYPE: DNA
<213> ORGANISM: Artificial
<220> FEATURE:
<223> OTHER INFORMATION: primer

<400> SEQUENCE: 55
aatacctttg gtttgctcat ggtatcgatt gttttagttt tgtttgtttg ttgtgtataa    60
cggg                                                                 64

<210> SEQ ID NO 56
<211> LENGTH: 64
<212> TYPE: DNA
<213> ORGANISM: Artificial
<220> FEATURE:
<223> OTHER INFORMATION: primer

<400> SEQUENCE: 56
cccgttatac acaacaaaca aacaaaacta aaacaatcga taccatgagc aaaccaaagg    60
tatt                                                                 64

<210> SEQ ID NO 57
<211> LENGTH: 35
<212> TYPE: DNA
<213> ORGANISM: Artificial
<220> FEATURE:
<223> OTHER INFORMATION: primer

<400> SEQUENCE: 57
actcagatct tcattatggc atgggaacag gagtt                               35

<210> SEQ ID NO 58
<211> LENGTH: 64
<212> TYPE: DNA
<213> ORGANISM: Artificial
<220> FEATURE:
<223> OTHER INFORMATION: primer

<400> SEQUENCE: 58
ccgtaagcaa aaatcttcat ggtatcgatt gttttagttt tgtttgtttg ttgtgtataa    60
cggg                                                                 64

<210> SEQ ID NO 59
<211> LENGTH: 64
<212> TYPE: DNA
<213> ORGANISM: Artificial
<220> FEATURE:
<223> OTHER INFORMATION: primer

<400> SEQUENCE: 59
cccgttatac acaacaaaca aacaaaacta aaacaatcga taccatgaag attttgctt     60 acgg                                                                 64

<210> SEQ ID NO 60
<211> LENGTH: 35
<212> TYPE: DNA
<213> ORGANISM: Artificial
<220> FEATURE:
<223> OTHER INFORMATION: primer

<400> SEQUENCE: 60
actcagatct tcattaatat tcaacagcaa tagct                               35

POLYPEPTIDE HAVING D-LACTATE DEHYDROGENASE ACTIVITY, POLYNUCLEOTIDE ENCODING THE POLYPEPTIDE, AND PROCESS FOR PRODUCTION OF D-LACTIC ACID

RELATED APPLICATIONS

This is a §371 of International Application No. PCT/JP2010/059306, with an international filing date of Jun. 2, 2010, which is based on Japanese Patent Application No. 2009-134213 filed on Jun. 3, 2009, the subject matter of which is incorporated by reference.

TECHNICAL FIELD

This disclosure relates to a novel polypeptide for production of D-lactic acid, which polypeptide has a D-lactate dehydrogenase activity; a polynucleotide encoding the polypeptide; and a transformant into which the polynucleotide is introduced. The disclosure also relates to a method of producing D-lactic acid which comprises culturing the transformant.

BACKGROUND

From the idea of carbon neutrality, strong attention has been given to polylactic acids (PLAs) which utilize a renewable resource, biomass, as starting material. PLAs are relatively low cost and heat resistant having a melting point of about 170° C.; therefore, they are expected as a biodegradable polymer which can be melt-molded. In addition, it is known that a stereocomplex polylactic acid can be obtained by mixing poly-L-lactic acid and poly-D-lactic acid (JP S61-36321A, JP S63-241024A and JP 2000-17163A). Stereocomplex polylactic acid are known to exhibit a higher melting point and higher crystallizability as compared to single polymers and provide useful molded articles as fibers, films and resin molded articles. For both of the starting materials thereof, L-lactic acid and D-lactic acid, there is a demand for a method of producing them with high purity and high efficiency.

In nature, there exist bacteria which efficiently produce lactic acids, such as lactic acid bacteria, and some of those lactic acid production methods utilizing such bacteria have already been put to practical use. Examples of bacteria which efficiently produce L-lactic acid include *Lactobacillus delbrueckii*. In addition, as bacteria which efficiently produce D-lactic acid, microbes such as *Sporolactobacillus laevolacticus* are known (WO 2007/043253). In any of these cases, the amount of the accumulated lactic acid reached a high level in anaerobic culture; however, since D-lactic acid and L-lactic acid are produced as by-product in L-lactic acid fermentation and D-lactic acid fermentation, respectively, the optical purity is lowered. In addition, it is extremely difficult to separate these lactic acids.

Therefore, as a production method of lactic acid having a high optical purity, it has been examined to introduce a gene encoding L-lactate dehydrogenase or D-lactate dehydrogenase into a yeast which does not intrinsically have lactic acid-producing ability and subject the yeast to L-lactic acid and D-lactic acid fermentation (WO 2007/043253, JP 2007-074939A, WO 2004/104202 and Ishida N, et al., *Journal of Bioscience and Bioengineering* (2006), 101, 172-7). With regard to L-lactic acid fermentation by genetically engineered yeast, by introducing a highly active gene originated from *Xenopus laevis* which encodes the L-lactate dehydrogenase, lactic acid fermentation can be efficiently performed with high optical purity (WO 2007/043253). On the other hand, with regard to D-lactic acid fermentation by genetically engineered yeast, although D-lactic acid having high optical purity can be obtained in the same manner as in the case of L-lactic acid fermentation, the yield thereof is a problem (JP 2007-074939A, WO 2004/104202 and Ishida N, et al., *Journal of Bioscience and Bioengineering* (2006), 101, 172-7).

It could therefore be helpful to provide highly productive D-lactic acid fermentation using a polypeptide having a D-lactate dehydrogenase activity higher than that of conventional polypeptides and a polynucleotide encoding the polypeptide.

SUMMARY

We studied a variety of D-lactate dehydrogenases and discovered a polypeptide which increases the production of D-lactic acid and also has a D-lactate dehydrogenase activity to yield only a small amount of by-product; and a polynucleotide encoding the polypeptide.

We thus provide:

(1) A polypeptide which is any one of the following (A) to (C):

(A) a polypeptide having the amino acid sequence shown in SEQ ID NO:1 or 2;

(B) a polypeptide having the same amino acid sequence as shown in SEQ ID NO:1 or 2 except that one or several amino acids are substituted, deleted, inserted and/or added, which polypeptide has a D-lactate dehydrogenase activity; and (C) a polypeptide having an amino acid sequence which has a sequence identity of not less than 80% to the amino acid sequence shown in SEQ ID NO:1 or 2, which polypeptide has a D-lactate dehydrogenase activity.

(2) A polynucleotide which is any one of the following (a) to (e):

(a) a polynucleotide having the nucleotide sequence shown in SEQ ID NO:3 or 4;

(b) a polynucleotide having the same nucleotide sequence as shown in SEQ ID NO:3 or 4 except that one or several nucleotides are substituted, deleted, inserted and/or added, which polynucleotide encodes a polypeptide having a D-lactate dehydrogenase activity;

(c) a polynucleotide which hybridizes under stringent conditions with the entirety or a part of the polynucleotide having the nucleotide sequence shown in SEQ ID NO:3 or 4 or a complementary strand thereof, which polynucleotide encodes a polypeptide having a D-LDH activity;

(d) a polynucleotide having a nucleotide sequence which has a sequence identity of not less than 80% to the nucleotide sequence shown in SEQ ID NO:3 or 4, which polynucleotide encodes a polypeptide having a D-lactate dehydrogenase activity; and (e) a polynucleotide encoding the polypeptide according to (1).

(3) A DNA construct in which the polynucleotide according to (2) and a promoter capable of expressing the polynucleotide are linked.

(4) The DNA construct according to (3), characterized in that the above-described promoter is a promoter of pyruvate decarboxylase 1 gene (PDC1 gene), suppression-of-exponential-defect 1 gene (SED1 gene) or glyceraldehyde-3-phosphate dehydrogenase 3 gene (TDH3 gene).

(5) The DNA construct according to (3) or (4), wherein the above-described promoter is selected from any one of the following (I) to (III):

(I) a promoter having the nucleotide sequence shown in any one of SEQ ID NOs:5 to 7;

(II) a promoter having a nucleotide sequence which hybridizes under stringent conditions with the nucleotide sequence shown in any one of SEQ ID NOs:5 to 7 or a nucleotide sequence comprising a part thereof; and (III) a promoter having the same nucleotide sequence as shown in any one of SEQ ID NOs:5 to 7 except that one or several nucleotides are deleted, substituted and/or added.

(6) A transformant in which the polynucleotide according to (2) or the DNA construct according to any one of (3) to (5) is introduced.

(7) A transformed yeast in which the polynucleotide according to (2) or the DNA construct according to any one of (3) to (5) is introduced.

(8) The transformed yeast according to (7), wherein at least one of pyruvate decarboxylase 1 gene (PDC1 gene), suppression-of-exponential-defect 1 gene (SED1 gene) and glyceraldehyde-3-phosphate dehydrogenase 3 gene (TDH3 gene) of the above-described transformed yeast is substituted with the polynucleotide according to (2) or the DNA construct according to any one of (3) to (5).

(9) The transformed yeast according to (8), wherein at least one of the above-described genes is PDC1 gene.

(10) A method of producing D-lactic acid, which comprises the step of culturing the transformant according to (6) or the transformed yeast according to any one of (7) to (9).

(11) A transformant in which a polynucleotide encoding D-lactate dehydrogenase originated from the family Limulidae or DNA construct in which the polynucleotide and a promoter capable of expressing the polynucleotide are linked is introduced.

(12) A transformed yeast in which a polynucleotide encoding D-lactate dehydrogenase originated from the family Limulidae or DNA construct in which the polynucleotide and a promoter capable of expressing the polynucleotide are linked is introduced.

(13) The transformed yeast according to (12), wherein at least one of pyruvate decarboxylase 1 gene (PDC1 gene), suppression-of-exponential-defect 1 gene (SED1 gene) and glyceraldehyde-3-phosphate dehydrogenase 3 gene (TDH3 gene) of the above-described transformed yeast is substituted with the above-described polynucleotide encoding D-lactate dehydrogenase originated from the family Limulidae or DNA construct in which the polynucleotide and a promoter capable of expressing the polynucleotide are linked is introduced.

(14) A method of producing D-lactic acid, which comprises the step of culturing the transformant according to (11) or the transformed yeast according to (12) or (13).

A polypeptide having a D-lactate dehydrogenase activity suitable for fermentative production of D-lactic acid and a polynucleotide encoding the polypeptide are provided. In addition, by using the polynucleotide, a transformant capable of highly producing D-lactic acid can be easily obtained, and in turn, D-lactic acid can be efficiently produced with high purity by culturing the transformant.

DETAILED DESCRIPTION

Figure 1:
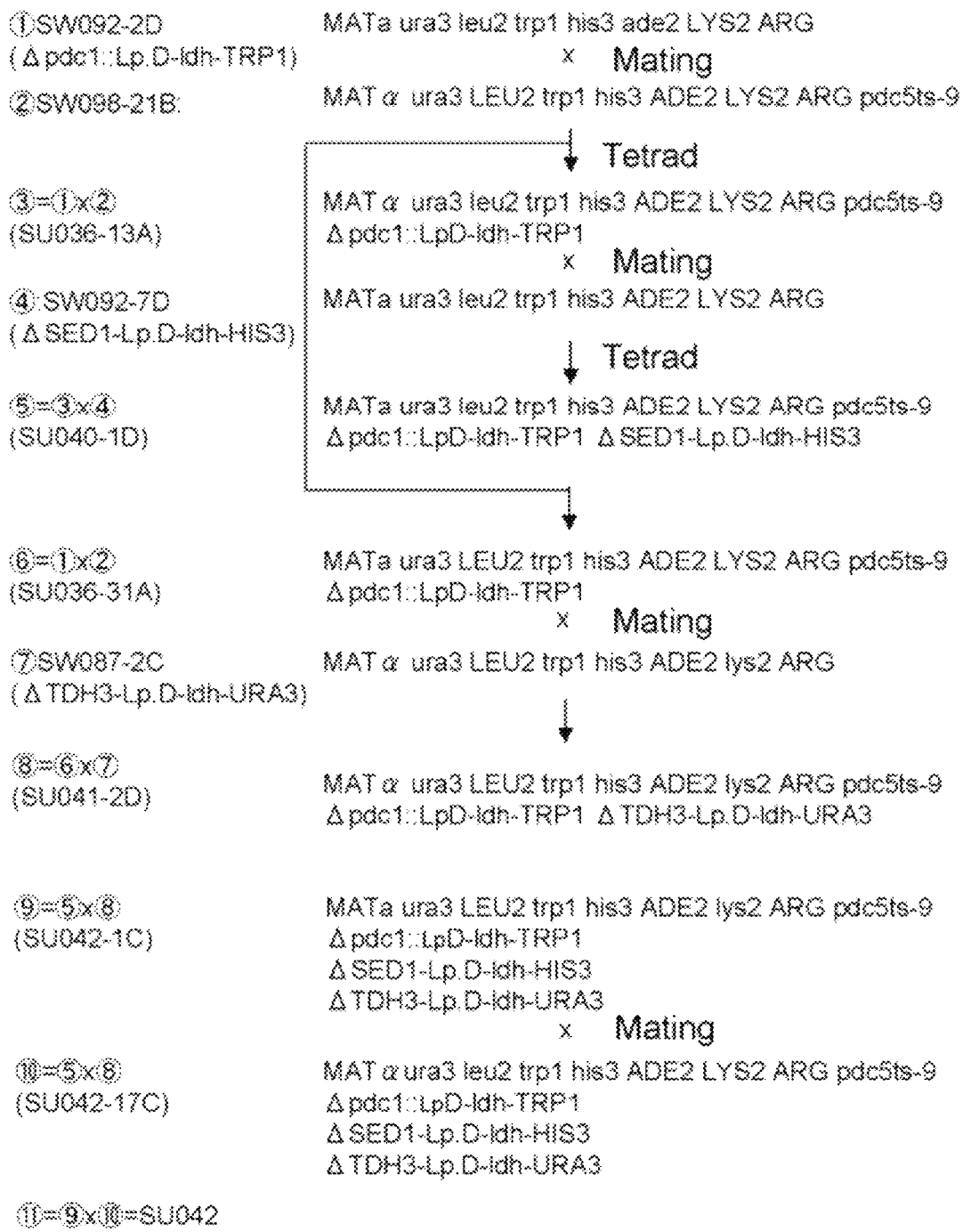
FIG. 1 shows the procedures for preparing one of the yeast SU042 strains.

The term "D-lactate dehydrogenase activity" (hereinafter, also referred to as "D-LDH") is an activity to convert reduced nicotinamide adenine dinucleotide (NADH) and pyruvic acid into D-lactic acid and oxidized nicotinamide adenine dinucleotide (NAD+).

We provide a polypeptide having the amino acid sequence shown in SEQ ID NO:1 or 2 or a homolog thereof, which polypeptide having a D-LDH activity.

The polypeptide having the amino acid sequence shown in SEQ ID NO:1 or 2 is a polypeptide originated from *Limulus polyphemus*, which belongs to the family Limulidae and genus *Limulus*.

Examples of the homolog of the polypeptide having the amino acid sequence shown in SEQ ID NO:1 or 2 include a polypeptide having the same amino acid sequence as shown in SEQ ID NO:1 or 2 except that one or several, preferably 1 to 10, more preferably 1 to 5, still more preferably 1 or 2 amino acids are substituted, deleted, inserted and/or added, which polypeptide also has a D-LDH activity.

Further, a homolog of the polypeptide shown in SEQ ID NO:1 or 2 may also be a polypeptide having an amino acid sequence which has a sequence identity of not less than 80%, preferably 90%, more preferably not less than 95% to the amino acid sequence shown in SEQ ID NO:1 or 2, which polypeptide also has a D-LDH activity. The sequence identity of an amino acid sequence can be easily checked using the BLAST, which is a software widely used in the art. Anyone can use the BLAST through the NCBI (National Center for Biotechnology Information) homepage, and the identity can be easily checked by using default parameters.

In addition, the homolog of the polypeptide having the amino acid sequence shown in SEQ ID NO:1 or 2 may also be a polypeptide originated from a living organism belonging to the family Limulidae, preferably a living organism belonging to the genus *Limulus* or *Tachypleus*, more preferably *Limulus polyphemus* belonging to the genus *Limulus*, or *Tachypleus tridentatus*, *Tachypleus gigas* or *Tachypleus rotundicauda* belonging to the genus *Tachypleus*, which polypeptide has a D-LDH activity.

The polypeptide having the amino acid sequence shown in SEQ ID NO:1 or 2 can be extracted from *Limulus polyphemus* by a known method or prepared using a known peptide synthesis method. Further, it can be also prepared by gene recombination technique using a polynucleotide encoding the amino acid sequence shown in SEQ ID NO:1 or 2. The polypeptide having the amino acid sequence shown in SEQ ID NO:1 or 2 can be also extracted from a living organism belonging to the genus *Tachypleus* by a known method or prepared using a known peptide synthesis method. Further, it can be also prepared by gene recombination technique using a polynucleotide encoding the amino acid sequence of the polypeptide.

The homolog of the polypeptide having the amino acid sequence shown in SEQ ID NO:1 or 2 may have an improved D-LDH activity and/or an improved thermal stability as compared to the polypeptide having the amino acid sequence shown in SEQ ID NO:1 or 2. The term "an improved D-LDH activity" refers to an improvement in the substrate affinity and molecular activity (Kcat) for pyruvic acid and NADH, as well as a shift in the optimum pH for the enzyme activity of the polypeptide closer to a pH suitable for growth of cells expressing the polypeptide. Such polypeptide may be artificially designed based on the polypeptide having the amino acid sequence shown in SEQ ID NO:1 or 2, or may be separated from nature. Further, a mutation may be randomly introduced to the D-lactate dehydrogenase gene by an evolutionary molecular engineering method to screen a preferred polypeptide therefrom.

We include a polynucleotide having the nucleotide sequence shown in SEQ ID NO:3 or 4 or a homolog thereof, which polynucleotide encodes a polypeptide having a D-LDH activity. The origin of the "polynucleotide" does not matter and may be a cDNA, genomic DNA, synthetic DNA, mRNA, synthetic RNA, replicon RNA; however, it is preferably a DNA or RNA, more preferably DNA. Also, the "polynucleotide" may be either single stranded or double stranded with a complementary strand thereof. Further, the "polynucleotide" may also contain a natural or artificial nucleotide derivative.

The polynucleotide having the nucleotide sequence shown in SEQ ID NO:3 or 4 is a polynucleotide originated from *Limulus polyphemus* and characterized by encoding a polypeptide having the above-described D-LDH activity.

Examples of the homolog of the polynucleotide shown in SEQ ID NO:3 or 4 include a polynucleotide having the same nucleotide sequence as shown in SEQ ID NO:3 or 4 except that one or several, preferably 1 to 40, more preferably 1 to 30, still more preferably 1 or 20, especially preferably 1 to 10, most preferably 1 to 5 nucleotides are substituted, deleted, inserted and/or added, which polynucleotide also encodes a polypeptide having a D-LDH activity.

Further, examples of the homolog of the polynucleotide shown in SEQ ID NO:3 or 4 also include a polynucleotide which hybridizes under stringent conditions with the entirety or a part of the polynucleotide having the nucleotide sequence shown in SEQ ID NO:3 or 4 or a complementary strand thereof, which polynucleotide also encodes a polypeptide having a D-LDH activity. The term "a polynucleotide which hybridizes under stringent conditions" refers to, for example, a polynucleotide which is hybridized by a known hybridization technique (*Current Protocols In Molecular Biology* edit. Ausubel et al., (1987) Publish. John Wily & Sons, Section 6.3-6.4) or the like using, as probe(s), one or a plurality of selected polynucleotides having at least 20, preferably 25, more preferably at least 30 arbitrary consecutive nucleotides of the original nucleotide sequence. Stringent conditions can be achieved, for example, by performing hybridization in the presence of 50% formamide at a hybridization temperature of 37° C., 42° C. for more stringent condition, 65° C. for still more stringent condition, and washing the resultant with a 0.1× to 2×SSC (saline-sodium citrate) solution (composition of 1×SSC solution: 150 mM sodium chloride and 15 mM sodium citrate).

Further, the homolog of the polynucleotide shown in SEQ ID NO:3 or 4 may also be a polynucleotide having a nucleotide sequence which has a sequence identity of not less than 80%, more preferably not less than 90%, still more preferably not less than 95% to the nucleotide sequence shown in SEQ ID NO:3 or 4, which polynucleotide also encodes a polypeptide having a D-LDH activity. The sequence identity of the nucleotide sequence of polynucleotide used herein can be determined by using the above-described gene analysis program BLAST or the like.

Further, the homolog of the polynucleotide shown in SEQ ID NO:3 or 4 may also be a polynucleotide originated from a living organism belonging to the family Limulidae, preferably a living organism belonging to the genus *Limulus* or *Tachypleus*, more preferably *Limulus polyphemus, Tachypleus tridentatus, Tachypleus gigas* or *Tachypleus rotundicauda*, which polynucleotide encodes a polypeptide having a D-LDH activity.

Although the above-described polynucleotide can be prepared by cloning from a living organism belonging to the family Limulidae, preferably a living organism belonging to the family Limulidae and genus *Limulus* (hereinafter, these are also collectively referred to as "*Limulus*"), it can also be synthesized chemically or by employing the technique of Fujimoto et al. (Hideya Fujimoto, *Production Method of Synthetic Gene, Plant Cell Engineering Series* 7, *Plant PCR Experimental Protocol*, 1997, Shujunsha Co., Ltd., p. 95-100), which is known as a synthesis method of long-chain DNA. Normally, the polynucleotide cloned from *Limulus* can be isolated by a known method. Examples of such method include one in which, using a primer synthesized based on a cDNA sequence which is highly conserved in the D-lactate dehydrogenase, the cDNA being prepared from poly A (+) RNA isolated from *Limulus* hemocytes, a partial fragment is amplified and sequenced, and the entire ORF sequence thereof is then determined by 5' RACE and 3' RACE methods, followed by amplification by PCR to obtain a polynucleotide. Further, the cloning from *Limulus* can also be performed by complementing the D-lactate dehydrogenase function. The principle thereof is described in detail in Dominique, G., *Appl Environ Microbiol*, United States (1995), 61, 266-272. In this manner, the polynucleotide having a nucleotide sequence once determined can be once again obtained from *Limulus* hemocytes. However, it can be also directly synthesized chemically using a DNA synthesis apparatus.

The above-described polypeptide or polynucleotide can be modified as appropriate by appropriately introducing a substitution(s), deletion(s), insertion(s) and/or addition mutation (s) to the amino acid sequence or nucleotide sequence thereof using a site-specific mutation introduction method (*Current Protocols In Molecular Biology* edit. Ausubel et al., (1987) Publish. John Wily & Sons Section 8.1-8.5) or the like. Further, such modification of an amino acid sequence of polypeptide or nucleotide sequence of polynucleotide is not restricted to those performed by artificial introduction or synthesis of a mutation, but encompasses not only those performed based on an artificial mutation treatment, but also those naturally occurred by a mutation in an amino acid.

The above-described polynucleotide can be used for preparation of a D-lactic acid-producing cell by gene recombination. For a host cell in which the polynucleotide is introduced by gene recombination (hereinafter, also referred to as "transformant") to become able to produce D-lactic acid, it is required that the polypeptide having a D-LDH activity which is encoded by the polynucleotide be expressed in the transformant. In this case, as a method of allowing the polypeptide having a D-LDH activity to be expressed, it is useful to utilize a DNA construct in which the polynucleotide and a promoter capable of expressing it are linked, that is, a DNA construct in which the polynucleotide is linked to the 3'-end of the promoter, and such DNA construct is also included. The DNA construct can be prepared by a method in which the polynucleotide (DNA) and a promoter capable of expressing the polynucleotide are each digested with an appropriate restriction enzyme(s) and then inserted to a restriction enzyme site or multicloning site of the below-described vector DNA to be linked or by linking the polynucleotide (DNA) and the promoter by performing PCR.

Preferably, the above-described DNA construct is carried by a vector such as a plasmid (DNA), bacteriophage (DNA), retrotransposon (DNA) or artificial chromosome (for example, YAC, PAC, BAC or MAC). Depending on the introduction mode of the DNA construct (inside or outside the host genome) and the type of the host cell, a prokaryotic vector, eukaryotic vector, animal cell vector or plant cell vector, which is known in the art, is selected as appropriate.

Examples of the plasmid include YCp-type *Escherichia coli*-yeast shuttle vectors such as pRS413, pRS415, pRS416, YCp50, pAUR112 and pAUR123; YEp-type *Escherichia* coli-yeast shuttle vectors such as pYES32 and YEp13; YIp-type *Escherichia coli*-yeast shuttle vectors such as pRS403, pRS404, pRS405, pRS406, pAUR101 and pAUR135; plasmids originated from *Escherichia coli* (for example, ColE-type plasmids such as pBR322, pBR325, pUC18, pUC19, pUC119, pTV118N, pTV119N, pBluescript, pHSG298, pHSG396 and pTrc99A; p1A-type plasmids such as pACYC177 and pACYC184; and pSC101-type plasmids such as pMW118, pMW119, pMW218 and pMW219); and plasmids originated from *Bacillus subtilis* (such as pUB110 and pTP5). Examples of the bacteriophage include λ-phages (such as Charon4A, Charon21A, EMBL3, EMBL4, λgt100, gt11 and zap), φX174, M13mp18 and M13mp19. An example of the retrotransposon is Ty factor and that of the YAC is pYACC2.

The "promoter" in the above-described DNA construct means a nucleotide sequence involved in the initiation of transcription of mRNA from a gene and normally refers to an upstream sequence of the 5'-end of the gene existing on the chromosome. The length of the promoter nucleotide sequence is preferably 1 to 3,000 bp, more preferably 1 to 1,000 bp; however, it is not particularly restricted as long as the nucleotide sequence can initiate the transcription of mRNA of the gene which exists in downstream. Further, a mutation and operation for improving the transcription activity of a promoter are known and the "promoter" also includes those which are modified by a known method. The promoter in the above-described DNA construct is not particularly restricted as long as it has a promoter activity in the transformant introduced with the DNA construct; however, as described below, since it is preferred that the DNA construct be introduced into a yeast, the promoter is preferably functional in the yeast.

Preferred examples of the promoter functioning in yeast include those of acid phosphatase gene (PHO5), glyceraldehyde-3-phosphate dehydrogenase genes (TDH1, 2 and 3), alcohol dehydrogenase genes (ADH1, 2, 3, 4, 5, 6 and 7), galactose metabolism-related genes (GAL1, 7 and 10), cytochrome c gene (CYC1), triosephosphate isomerase gene (TPI1), phosphoglycerate kinase gene (PGK1), phosphofructose kinase gene (PFK1) and pyruvate decarboxylase genes (PDC1, 5, 6), as well as those promoters of enolase-1 gene (ENO1), cell wall-related protein 2 gene (CWP2) and suppression-of-exponential-defect 1 gene (SED1) which are described and used in the international application PCT/JP2008/072129 and exhibit a gene expression amount of not less than 5 times of the average relative expression amount of all genes after 50 hours or later from the start of yeast culture.

More preferred examples of the promoter functioning in yeast include the PDC1 promoter and TDH3 promoter which are highly expressed in the ethanol fermentation pathway of yeast; and the SED1 promoter which is highly expressed in a yeast cultured for a prolonged period, and more specific examples include the PDC1 promoter shown in SEQ ID NO:5, the SED1 promoter shown in SEQ ID NO:6 and the TDH3 promoter shown in SEQ ID NO:7.

Further, the PDC1 promoter, SED1 promoter or TDH3 promoter may also have, as long as its promoter activity is maintained, the same nucleotide sequence as shown in one of SEQ ID NOs:5 to 7, respectively, except that one or several, preferably 1 to 40, more preferably 1 to 30, still more preferably 1 or 20, especially preferably 1 to 10, most preferably 1 to 5 nucleotides are deleted, substituted and/or added.

Further, the PDC1 promoter, SED1 promoter or TDH3 promoter may also have, as long as its promoter activity is maintained, a nucleotide sequence which hybridizes under stringent conditions with a nucleotide sequence containing the nucleotide sequence shown in one of SEQ ID NOs:5 to 7 or a part thereof, respectively. A nucleotide sequence which "hybridizes under stringent conditions" refers to, for example, a polynucleotide which is hybridized by a known hybridization technique (*Current Protocols In Molecular Biology* edit. Ausubel et al., (1987) Publish. John Wily & Sons, Section 6.3-6.4) or the like using, as probe(s), one or a plurality of selected polynucleotides having at least 20, preferably 25, more preferably at least 30 arbitrary consecutive nucleotides of the original nucleotide sequence. Stringent conditions can be achieved, for example, by performing hybridization in the presence of 50% formamide at a hybridization temperature of 37° C., 42° C. for more stringent condition, 65° C. for still more stringent condition, and washing the resultant with a 0.1× to 2×SSC (saline-sodium citrate) solution (composition of 1×SSC solution: 150 mM sodium chloride and 15 mM sodium citrate).

We also include a transformant obtained by introducing the above-described polynucleotide or DNA construct into a host cell. The host cell is not particularly restricted as long as it stably retains the polynucleotide or DNA construct and examples thereof include bacteria such as *Escherichia coli*, *Bacillus subtilis* and lactic acid bacteria; yeast; insect cells; animal cells; and plant cells, and yeast is preferably used since it is acid-resistant and capable of growing even when D-lactic acid is highly produced by expressing a polypeptide having a D-LDH activity.

Examples of the yeast include those belonging to the genera *Saccharomyces, Schizosaccharomyces, Kluyveromyces, Candida, Pichia, Hansenura, Yarrowia, Zygosaccharomyces, Torulopsis, Debaryomyces, Issachenkia* and *Fellomyces*. However, preferably, the yeast is one belonging to the genus *Saccharomyces, Candida* or *Kluyveromyces*, more preferably *Saccharomyces cerevisiae, Candida utilis, Candida glabrata, Candida albicans, Candida boidinii, Candida sonorensis, Kluyveromyces lactis* or *Kluyveromyces marxianus*.

Further, a polyploid yeast is preferably used since it can stably maintain a high productivity of D-lactic acid over a prolonged period under simple operating conditions, so that D-lactic acid can be stably produced at a low cost. The term "polyploid yeast" refers to yeast having 2 or more sets of chromosomes in the cell. The number of sets of chromosomes in the polyploid yeast is not particularly restricted; however, diploid yeast having 2 sets of chromosomes is preferred. Examples of the polyploid yeast include baker's yeasts, sake yeasts, wine yeasts and beer yeasts that are frequently used in the fermentation industry. The polyploid yeast to be used may be one isolated from a natural environment or one whose properties are partially modified by mutation or gene recombination.

Further, a prototrophic yeast is preferably used since it not only allows the use of a culture medium containing less nutrients than conventional media, that is, a low-cost medium, but also enables stable maintenance of a high productivity of D-lactic acid over a prolonged period under simple operating conditions, so that lactic acid can be stably produced at a low cost. The term "auxotrophic" means that a mutation occurred in a nutrient-synthesis gene of the wild-type yeast for some reason, resulting in a deficiency in the capacity to synthesize the nutrient. That is, "prototrophic yeast" is one which does not have genotype exhibiting auxotrophy or one in which such genotype is complemented. Examples of a method for preparing a prototrophic yeast by reverting the auxotrophy of an auxotrophic yeast include a method in which an auxotrophy is reverted by introducing a nutrient-synthesis gene by a gene recombination technique; and a method in which the processes of mating yeasts having different auxotrophies with each other, allowing ascus formation and reverting a target auxotrophy are repeated until all of the auxotrophies are eventually reverted to obtain a prototrophic yeast. It is noted here that whether or not a yeast is prototrophic can be judged based on whether or not the yeast is capable of growing in SD medium, which is a minimal medium for yeasts.

Further, yeast is a microorganism which vigorously performs ethanol fermentation, and in the metabolic pathway thereof, pyruvic acid which is a glycolytic product is converted to acetaldehyde by pyruvate decarboxylase, which is then converted to ethanol by alcohol dehydrogenase. Therefore, it is preferred that a yeast strain in which the pyruvate decarboxylase gene serving as the starting point of the ethanol metabolic pathway is destructed be used as host since this allows pyruvic acid, which should be naturally metabolized in the ethanol metabolic pathway, to be used in the D-lactic acid metabolic pathway.

Particularly in the case of *Saccharomyces cerevisiae*, there are three types of genes encoding a pyruvate decarboxylase: pyruvate decarboxylase 1 (PDC1) gene, pyruvate decarboxylase 5 (PDC5) gene and pyruvate decarboxylase 6 (PDC6) gene. Among these genes, only the PDC1 and PDC5 are considered to have pyruvate dehydrogenase activity in the yeast cell; therefore, it is preferred that a strain having destructed PDC1 gene or PDC5 gene be used and it is more preferred that a strain having destructed PDC1 gene be used. In addition, as described in JP 2008-048726A, in the strain having destructed PDC1 gene, a strain having a mutant-type PDC5 gene which includes a mutation resulting in a decrease in the PDC5 activity is preferred, and a strain having a temperature-sensitive mutant-type PDC5 gene is more preferred. The "temperature-sensitive mutant-type PDC5 gene" refers to a mutant-type PDC5 which has a property to exhibit a pyruvate decarboxylase activity comparable to that of the wild-type PDC5 at a certain culturing temperature, but exhibit a deletion of or decrease in the PDC5 activity when the culturing temperature is changed to not lower than the certain culturing temperature. The normal culturing temperature of *Saccharomyces cerevisiae* is 28 to 30° C. and it is preferred that the temperature at which such temperature sensitivity is exhibit be close to the normal culturing temperature since this makes the amount of heat required for changing the culturing temperature smaller, so that the culturing cost can be reduced. In particular, it is preferred that the temperature-sensitive mutant-type PDC5 exhibit the temperature sensitivity at a temperature of not lower than 34° C.

Examples of a method of allowing a polypeptide having a D-LDH activity to be expressed in a transformed yeast by introducing the above-described polynucleotide or DNA construct to the yeast include, as already described, a method in which a vector containing the DNA construct is extrachromosomally introduced into a yeast and a method in which the polynucleotide or DNA construct is introduced into a yeast chromosome, and both of these method can be employed.

In the method of introducing the above-described polynucleotide into a yeast chromosome, a construct which contains the polynucleotide and a DNA segment for homologous recombination whose sequence is homologous to that of the yeast chromosome (hereinafter, also referred to as "DNA construct for homologous recombination") can be preferably used. The DNA segment for homologous recombination has a DNA sequence which is homologous to the one in the vicinity of the target site in the yeast chromosome to which the polynucleotide is to be introduced. The construct contains at least one, preferably two such DNA segments for homologous recombination. In cases where the construct contains two DNA segments for homologous recombination, it is preferred that the two DNA segments for homologous recombination each have a DNA sequence homologous to the DNA of the upstream or downstream of the target site located on the chromosome and that the polynucleotide be linked between these DNA segments.

The method of performing homologous recombination using the DNA construct for homologous recombination is not particularly restricted, and a method in which the DNA construct for homologous recombination is amplified by PCR and the resulting PCR fragment is inserted into a plasmid which is then introduced into a yeast or a method in which the PCR fragment is introduced into a yeast can be employed. Further, it is preferred that the DNA construct for homologous recombination contain a terminator for regulating the expression of the polynucleotide. The "terminator" means a sequence which terminates mRNA transcription from a gene and normally refers to a downstream sequence of the 3'-end of the gene existing on the chromosome.

In addition, it is preferred that the DNA construct for homologous recombination contain, in addition to the polynucleotide or DNA construct, a selective marker for making the selection of transformed yeast easy. Examples of the selective marker used herein include auxotrophic complementary genes such as URA3 and TRP1 and drug-resistant genes such as G418-resistant gene and neomycin-resistant gene.

A DNA construct for homologous recombination containing the above-described polynucleotide, terminator and selective marker can be prepared by PCR in accordance with, for example, the following steps 1 to 3.

Step 1: Using a plasmid in which a terminator is linked to downstream of the polynucleotide as template and primers 1 and 2 as primer set, a fragment containing the polynucleotide and the terminator is amplified by PCR. The primer 1 is designed in such a manner to add a sequence of not less than 40 b complementary to the upstream of the introduction target site, and the primer 2 is designed based on a sequence originated from the plasmid which is located the downstream of the terminator.

Step 2: Using a plasmid having a selective marker such as pRS400, pRS424 or pRS426 as template and primers 3 and 4 as primer set, a fragment containing the selective marker is amplified by PCR. The primer 3 is designed in such a manner to add a sequence of not less than 30 bp which has a homology to a sequence located downstream of the terminator of the PCR fragment obtained in the step 1, and the primer 4 is designed in such a manner to add a sequence of not less than 40 bp corresponding to the downstream of the introduction target site.

Step 3: Using a mixture of the PCR fragments obtained in the steps 1 and 2 as template and primers 1 and 4 as primer set, PCR is performed to obtain a DNA construct for homologous recombination containing the polynucleotide, terminator and yeast selective marker, in which sequences corresponding to the upstream and downstream of the introduction target site are added to both respective ends.

To introduce the above-described DNA construct for homologous recombination into a yeast, a method such as transfection, cotransfection or electroporation can be employed. Specific examples thereof include a method using lithium acetate and protoplast method.

When introducing the above-described polynucleotide into a yeast chromosome by homologous recombination, the introduction is carried out such that the polynucleotide can be regulated by a promoter of an endogenous gene located on the yeast chromosome. In this case, by the introduction of the above-described polynucleotide, the endogenous gene to be naturally regulated by the promoter may be simultaneously destructed and the exogenous polynucleotide may be expressed in place of this endogenous gene. This method is particularly useful when the promoter is a high-expression promoter in yeast as described in the above and when an endogenous gene functioning to inhibit the D-lactic acid metabolic pathway of yeast is to be destructed.

Preferred examples of the endogenous gene which serves as a target when introducing the above-described polynucleotide into a yeast chromosome include acid phosphatase gene (PHO5), glyceraldehyde-3-phosphate dehydrogenase genes (TDH1, 2 and 3), alcohol dehydrogenase genes (ADH1, 2, 3, 4, 5, 6 and 7), galactose metabolism-related genes (GAL1, 7 and 10), cytochrome c gene (CYC1), triosephosphate isomerase gene (TPI1), phosphoglycerate kinase gene (PGK1), phosphofructose kinase gene (PFK1) and pyruvate decarboxylase genes (PDC1, 5, 6), as well as promoters of enolase-1 gene (ENO1), cell wall-related protein 2 gene (CWP2) and suppression-of-exponential-defect 1 gene (SED1) which are described and used in the international application PCT/JP2008/072129 and exhibit a gene expression amount of not less than 5 times of the average relative expression amount of all genes after 50 hours or later from the start of yeast culture. In particular, more preferred examples include the PDC1 gene and TDH3 gene which are highly expressed in the ethanol fermentation pathway of yeast; and the SED1 gene which is highly expressed in a yeast cultured for a prolonged period. As described in the above, it is still more preferred that the above-described polynucleotide be introduced in such a manner to destruct at least the PDC1 gene serving as the starting point of the ethanol fermentation pathway or PDC5 gene, preferably the PDC1 gene, since this allows pyruvic acid metabolized in the ethanol metabolic pathway to be used in the D-lactic acid metabolic pathway.

Further, as the method of introducing the above-described DNA construct into a yeast chromosome, in the same manner as in the case of introducing the above-described polynucleotide into a yeast chromosome, a DNA construct for homologous recombination can be prepared and introduced at an intended site located on the chromosome by homologous recombination. It is noted here that, since the above-described DNA construct already contains a promoter capable of expressing the above-described polynucleotide, it is not necessary to carry out the introduction of the DNA construct in such a manner that the above-described polynucleotide can be regulated by a promoter of an endogenous gene located on the yeast chromosome.

Whether or not the above-described polynucleotide or DNA construct was introduced at the desired position on the yeast chromosome can be confirmed by PCR or Southern hybridization method. For example, the confirmation can be carried out by preparing a DNA from a transformed yeast and performing PCR with an introduction site-specific primer, followed by detection of the expected band by performing electrophoresis for the resulting PCR product. Alternatively, the confirmation can be carried out by performing PCR with a primer labeled with a fluorescent dye or the like. These methods are known to those skilled in the art.

We also provide a method of producing D-lactic acid which comprises the step of culturing the above-described transformant. When the above-described transformant is cultured, expression of a polypeptide having a D-LDH activity is newly provided or enhanced in the transformant and, thus, D-lactic acid metabolic pathway is newly provided or enhanced. As a result, D-lactic acid can be obtained by carrying out the step of separating D-lactic acid from the culture. The term "culture" used herein encompasses a culture supernatant, as well as transformant and homogenate thereof.

The method of culturing the above-described transformant is not particularly restricted and a known method is employed. For example, as the method of culturing the above-described transformed yeast, one described in M. D. Rose et al., "Methods In Yeast Genetics", Cold Spring Harbor Laboratory Press (1990) or the like can be employed. In cases where a plasmid containing the above-described DNA construct or DNA construct for homologous recombination contains a selective marker, by culturing the above-described transformant in a nutrient-free medium or drug-supplemented medium depending on the selective marker, a desired transformant can be selected.

As the medium in which the above-described transformant is cultured, as long as it contains a carbon source, nitrogen source, inorganic salts and the like that can be utilized by the transformant and enables efficient culturing thereof, any natural medium or synthetic medium can be used. For example, in the case of a transformed yeast, as the carbon source, carbohydrates such as glucose, fructose, sucrose, galactose, maltose, raffinose, trehalose, sorbose, cellobiose, lactose, melibiose, melezitose, inulin, xylose, arabinose, ribose, rhamnose, glucosamine, erythritol, ribitol, mannitol, glucitol, salicin and starch; organic acids such as acetic acid, propionic acid and citric acid; and alcohol such as ethanol and propanol can be used. As the nitrogen source, in addition to ammonium salts of an inorganic or organic acid such as ammonia, ammonium chloride, ammonium sulfate, ammonium acetate and ammonium phosphate and other nitrogen-containing compounds, peptone, meat extract, corn steep liquor and the like can be used. As inorganic compound, monopotassium phosphate, magnesium phosphate, magnesium sulfate, sodium chloride, ferrous sulfate, manganese sulfate, copper sulfate, calcium carbonate and the like can be used.

In the culturing of the above-described transformant, usually, the condition thereof is set to one in which good lactic acid productivity is attained, ranging from an aerobic condition, such as culture with shaking or culture with aeration and stirring, to an anaerobic condition where aeration is not performed, and the culturing is preferably carried out under a microaerobic condition or anaerobic condition. The culturing can be carried out at a culturing temperature of 25 to 37° C. However, a temperature of 28 to 35° C. is preferred. Since the pH of the culture decreases as D-lactic acid is accumulated in the medium, it can be also neutralized by an alkaline substance such as calcium hydroxide, calcium carbonate, sodium hydroxide, potassium hydroxide, aqueous ammonia or ammonia gas. Further, to facilitate the subsequent purification of lactic acid, the culturing can be also carried out without such neutralization. Moreover, the culturing method is not particularly restricted as long as it can fermentatively produce D-lactic acid of interest, and batch culture, fed-batch culture, chemostat culture, continuous culture or the like can be employed. Preferably, the culturing is carried out by batch culture or the continuous culture using a membrane described in WO 2007/097260, where fermentation culture is separated into a filtrate and non-filtrate using a separation membrane not liable to clogging and a desired fermentation product is collected from the filtrate, and at the same time, the non-filtrate is retained in or refluxed to the fermentation culture.

The method of measuring D-lactic acid obtained in the above-described culture is not particularly restricted, and examples thereof include a method using HPLC and a method using the F-kit (manufactured by Roche).

The D-lactic acid contained in the above-described fermentation culture can be separated and purified by a combination of those conventionally known methods of concentration, distillation, crystallization and the like, and examples thereof include a method in which the pH of filtered and separated fermentation liquid is adjusted to not higher than 1, followed by extraction with diethyl ether, ethyl acetate or the like; a method in which lactic acid is allowed to adsorb to an ion-exchange resin followed by washing and elution; a method in which lactic acid is allowed to react with an alcohol in the presence of an acid catalyst to obtain an ester, which is then distilled; a method in which lactic acid is crystallized in the form of a calcium salt or lithium salt; and a separation and purification method in which the nanofilter disclosed in WO 2009/004922 and distillation are used in combination.

EXAMPLES

Our polypeptides, polynucleotides and processes will now be described by way of examples. However, this disclosure is not restricted thereto.

Example 1

Nucleotide Sequencing of Polynucleotides Originated from *Limulus polyphemus* which Encode a Polypeptide having a D-LDH Activity (Hereinafter, Referred to as "D-LDH Genes Originated from *Limulus polyphemus*")

For preparation of cDNAs of *Limulus polyphemus*, polyA (+) RNA was purified. The polyA (+) RNA was isolated from the hemocytes of *Limulus polyphemus*. Total RNA was separated from the hemocytes of *Limulus polyphemus* (purchased from Marine Biological Laboratory (USA)) in accordance with the AGPC method (see *Experimental Medicine* Vol. 9 (1991), p. 1937-1940). The polyA (+) RNA was isolated from the thus separated total RNA using "Oligotex-dT30 Super Kit" (manufactured by Takara Bio Inc.). Next, using "SuperScript II Reverse Transcriptase" (Manufactured by Invitrogen) and oligo d (T) as primer, cDNAs were synthesized. Then, using the thus obtained reaction solution as template and the oligo DNAs shown in SEQ ID NOs:8 and 9 as primers, which oligo DNAs were designed with attention given to the DNA sequences highly conserved in the D-LDH genes, PCR was performed to amplify partial sequences of the D-LDH genes originated from *Limulus polyphemus*. The PCR was performed under the following conditions: 95° C. (3 minutes); {95° C. (30 seconds)–45° C. (30 seconds)–72° C. (30 seconds)}×35 cycles; 72° C. (5 minutes). Thereafter, the thus amplified DNA fragments were verified by electrophoresis using 1.0% agarose gel, and after purifying an amplified fragment of 600 bp using "QIA quick Gel extraction kit" (manufactured by Qiagen), this fragment was cloned into a plasmid vector "pGEMt-easy" (manufactured by Promega) and the DNA was sequenced. The nucleotide sequencing was performed using "Taq DyeDeoxy Terminator Cycle Sequencing Kit" (manufactured by Applied Biosystems) in accordance with Sanger's method. As a result, two kinds of partial sequences (D-LDH1 and D-LDH2) which are thought to correspond to the D-LDH genes originated from *Limulus polyphemus* were obtained.

Next, using 5' RACE and 3' RACE methods, the entire ORF sequences of the D-LDH1 and D-LDH2 were clarified. The 5' RACE was performed by the following method. First, 50 µL of the oligo DNA shown in SEQ ID NO:10 (for D-LDH1) or SEQ ID NO:11 (for D-LDH2) which was adjusted to 100 µM, 50 units of T4 polynucleotide kinase (manufactured by Takara Bio Inc.), 10 µL of 10× kinase buffer (500 mM Tris-HCl pH7.6, 100 mM $MgCl_2$, 50 mM DTT, 1 mM spermidine, 1 mM EDTA), 1 µL of 100 mM ATP and 34 µL of distilled water were mixed and left to stand at 37° C. for 1 hour to phosphorylate the 5'-end of the oligo DNA, and this oligo DNA was purified by performing a phenol-chloroform-isoamyl alcohol treatment and ethanol precipitation. Next, using the polyA (+) RNA of *Limulus polyphemus* as template, "SuperScript II Reverse Transcriptase" (manufactured by Invitrogen) and the above-described phosphorylated oligo DNA as primers, cDNA was synthesized. Thereafter, single-stranded cDNA was concatemerized by ligation reaction using "5'-Full RACE Core Set" (manufactured by Takara Bio Inc.) and the first PCR was performed using the thus produced concatemerized cDNA as template and the oligo DNAs shown in SEQ ID NOs:12 and 13 (for D-LDH1) or those shown in SEQ ID NOs:14 and 15 (for D-LDH2) as primers. Further, the second PCR was performed using the resulting reaction solution as template and the oligo DNAs shown in SEQ ID NOs:16 and 17 (for D-LDH1) or those shown in SEQ ID NOs:18 and 19 (for D-LDH2) as primers. The verification and purification of the amplified fragments and the nucleotide sequencing thereof were performed as described in the above.

The 3' RACE was performed by the following method. First, using the polyA (+) RNA of *Limulus polyphemus* as template, "SuperScript II Reverse Transcriptase" (manufactured by Invitrogen) and oligo d (T) as primer, cDNA was synthesized. Next, using this reaction solution as template and the oligo d (T) and the oligo DNA shown in SEQ ID NO:13 (for D-LDH1) or SEQ ID NO:15 (for D-LDH2) as primers, the first PCR was performed. Further, the second PCR was performed using the resulting reaction solution as template and the oligo d (T) and the oligo DNA shown in SEQ ID NO:17 (for D-LDH1) or SEQ ID NO:19 (for D-LDH2) as primers. The verification and purification of the amplified fragments and the nucleotide sequencing thereof were performed as described in the above.

The amino acid sequence (SEQ ID NO:1) of the D-LDH1 gene originated from *Limulus polyphemus* and the cDNA ORF sequence (SEQ ID NO:3), or the amino acid sequence (SEQ ID NO:2) of the D-LDH2 and the cDNA ORF sequence (SEQ ID NO:4) were determined by ligating the sequences obtained in the above-described method. It is noted here that the sequence identities between the amino acid sequences shown in SEQ ID NOs:1 and 2 and between the nucleotide sequences shown in SEQ ID NOs:3 and 4 were determined by BLAST to be 93% and 82%, respectively.

Example 2

Construction of a Plasmid Expressing the D-LDH Genes Originated from *Limulus polyphemus*

Using, as a primer set, the oligo DNAs shown in SEQ ID NOs:20 and 21 or those shown in SEQ ID NOs:22 and 23, which respectively correspond to the ORF 5'-side and ORF 3'-side of the D-LDH1 gene and D-LDH2 gene which were sequenced in Example 1 and are thought to be the D-LDH genes originated from *Limulus polyphemus* (hereinafter, referred to as "Lp. D-LDH1 gene" and "Lp. D-LDH2 gene", respectively) and, as template, the cDNA synthesized from the poly A (+) RNA of *Limulus polyphemus*, PCR was performed to clone the genes. The thus obtained DNA fragments were digested with restriction enzymes XhoI and NotI and introduced into the cleavage sites of yeast expression vector pTRS11 (carrying TDH3 promoter and selective marker URA3 gene; see JP 2006-280368A: it is noted here that, therein, the TDH3 promoter and terminator are indicated as GAPDH promoter and terminator), which was digested in the same manner with the restriction enzymes XhoI and NotI, to prepare plasmid vectors containing a DNA construct in which the TDH3 promoter and the Lp. D-LDH1 gene or Lp. D-LDH2 gene are linked. Hereinafter, these plasmid vectors are referred to as "pTRS205" (carrying the Lp. D-LDH1) and "pTRS206" (carrying the Lp. D-LDH2). The pTRS11 vector was prepared by digesting pNV11 vector (see Nature, vol. 357, 25 Jun. 1992, p. 700) with the restriction enzyme XhoI and, after removing inserts, allowing it to self-ligate.

Example 3

Introduction of the Plasmid Expressing the D-LDH Genes Originated from *Limulus polyphemus* into Yeast The pTRS205 and pTRS206 obtained as described in Example 2 were introduced into the yeast *Saccharomyces cerevisiae* SW029-1B strain (genotype: MATa ura TRP (Δpdc1::TRP1) his ade lys leu) (hereinafter, referred to as "SW029-1B strain"). The introduction of the plasmids was carried out by a lithium acetate method using "YEAST-MAKER Yeast Transformation System" (manufactured by Clonetech) (for details, see the attached protocol). The SW029-1B strain used as the host is a strain which lacks uracil synthesis capacity and, by the action of the selective marker URA3 gene of the pTRS205 and 206, transformed yeast into which the pTRS205 and pTRS206 were introduced can be selected on a uracil-free medium. The introduction of the D-LDH gene-expressing vectors into the transformants obtained in this manner was confirmed by extracting genomic DNA containing plasmid DNA from the transformants cultured in a uracil-free liquid medium using a genomic DNA extraction kit "Dr. GenTLE" (manufactured by Takara Bio Inc.) and performing PCR using the thus extracted genomic DNA as template. As primers, those which were used for cloning the D-LDH genes originated from *Limulus polyphemus* were employed, respectively. As a result, it was confirmed that each of the D-LDH genes originated from *Limulus polyphemus* were respectively introduced into all of the transformed yeast cells.

Example 4

D-lactic Acid Productivity Test 1

Using the *Saccharomyces cerevisiae* SW029-1B strains obtained as described in Example 3 into which the pTRS205 and 206 were introduced (hereinafter, referred to as "SW029-1B/pTRS205 strain" and "SW029-1B/pTRS206 strain", respectively), D-lactic acid productivity test was carried out. SC3 medium having the composition shown in Table 1 from which uracil was removed (SC3-Ura medium) was added in test tubes in an amount of 10 mL. A small amount of each strain was inoculated thereto and cultured overnight at 30° C. (preculture). Next, 10 mL of SC3-Ura medium was added in test tubes and 100 μL of each of the thus obtained preculture media was inoculated thereinto, followed by culturing at 30° C. with shaking (main culture). After 40 hours since the start of the main culture, the culture media were centrifuged and lactic acid contained in the resulting supernatants was measured by HPLC under the following conditions:

Column: "Shim-Pack SPR-H" (manufactured by Shimadzu Corporation)
Mobile phase: 5 mM p-toluenesulfonic acid (flow rate=0.8 mL/min)
Reaction solution: 5 mM p-toluenesulfonic acid, 20 mM Bistris, 0.1 mM EDTA·2Na (flow rate=0.8 mL/min)
Detection method: electroconductivity
Temperature: 45° C.

In addition, based on the results of measuring the D-lactic acid and L-lactic acid concentrations by HPLC method under the following conditions, the optical purity of D-lactic acid was calculated using the following equations.

Column: "TSK-gel Enantio L1" (registered trademark: manufactured by Tosoh Corporation)
Mobile phase: 1 mM aqueous copper sulfate solution
Flow rate: 1.0 ml/min
Detection method: UV 254 nm
Temperature: 30° C.
Optical purity (% e.e.)=100×(D−L)/(D+L)
Optical purity (%)=100×D/(D+L)

In the above equations, L represents the concentration of L-lactic acid and D represents the concentration of D-lactic acid.

TABLE 1

| Glucose | 100 g/L |
| Ammonium sulfate | 1.5 g/L |
| Yeast Nitrogen base w/o amino acid and ammonium sulfate (manufactured by Difco) | 1.7 g/L |
| 19 standard amino acids other than leucine | 152 mg/L |
| Leucine | 760 mg/L |
| Inositol | 152 mg/L |
| p-aminobenzoate | 16 mg/L |
| Adenine | 40 mg/L |
| Uracil | 152 mg/L |

As a result, the concentration of the accumulated D-lactic acid was 13 g/L for the SW029-1B/pTRS205 strain and 12 g/L for the SW029-1B/pTRS206 strain. In addition, only D-lactic acid was detected in the culture media and the level of L-lactic acid was not higher than the detection limit. It was confirmed that the transformed yeast was able to produce D-lactic acid by introducing thereinto the D-LDH genes cloned from *Limulus polyphemus*.

Example 5

Introduction of the D-LDH Genes Originated from *Limulus polyphemus* into Yeast Chromosome By the following steps 1 to 3, a DNA construct for homologous recombination which contains the D-LDH genes originated from *Limulus polyphemus* was prepared.

[Step 1]

Using the pTRS205 carrying the Lp. D-LDH1 gene and the pTRS206 carrying the Lp. D-LDH2 gene that were obtained in Example 2 as templates and the oligo DNAs shown in SEQ ID NOs:24 and 25 or those shown in SEQ ID NOs:26 and 25 as primer set, PCR was performed to amplify DNA fragments of about 1.1 kb containing each of the D-LDH genes. The oligo DNAs shown in SEQ ID NOs:24 and 26 were designed in such a manner that a sequence having a homology to the 65 bp region upstream of the PDC1 gene is added.

[Step 2]

Next, using the plasmid pRS424 (GenBank Accession Number: U03453) as template and the oligo DNAs shown in SEQ ID NOs:27 and 28 as primer set, PCR was performed to amplify a DNA fragment of about 1.4 kb containing the TRP1 gene, which is a yeast selection marker. The oligo DNA shown in SEQ ID NO:28 was designed in such a manner that a sequence having a homology to the 65 bp region downstream of the PDC1 gene is added.

[Step 3]

After separating the DNA fragments by 1% agarose gel electrophoresis, they were purified using "QIA quick Gel extraction kit" (manufactured by Qiagen). Using a mixture of the thus obtained 1.1 kb fragments containing the respective D-LDH genes and 1.4 kb fragment containing the TRP1 gene as template and the oligo DNAs shown in SEQ ID NOs:24 and 28 or those shown in SEQ ID NOs:26 and 28 as primer set, PCR was performed to amplify a DNA construct of about 2.5 kb used for homologous recombination in which each of the D-LDH genes, TDH3 terminator and TRP 1 gene were linked.

The DNA construct for homologous recombination prepared in the above-described manner was transformed into Saccharomyces cerevisiae SW092-2D strain (hereinafter, referred to as "SW092-2D strain"), which is a Saccharomyces cerevisiae NBRC10505 strain (hereinafter, referred to as "NBRC10505 strain") in which the lysine auxotrophy is reverted.

The SW092-2D strain was prepared by the following method. Using the genomic DNA of the Saccharomyces cerevisiae BY4741 strain manufactured by Funakoshi Corporation as template and the oligonucleotides (SEQ ID NOs:29 and 30) as primer set, PCR was performed to amplify a PCR fragment of about 2 kb corresponding to the former half of the LYS2 gene. After separating the PCR fragment by 1% agarose gel electrophoresis and purifying it in accordance with a conventional method, the PCR fragment was transformed into the NBRC10505 strain to cancel the amber mutation in the LYS2 gene. By culturing the yeast strain in a lysine-free medium, a transformant in which the lysine synthesis capacity was reverted (NBRC10505(LYS2) strain) was selected. To confirm that the thus obtained transformant is a yeast in which the amber mutation in the LYS2 gene was canceled, the following steps were carried out. First, diploid cells were obtained by mating the thus obtained transformant with the Saccharomyces cerevisiae LOGY7 strain having the wild-type LYS2 gene and the diploid cells were cultured in an ascus formation medium to allow ascus formation. The resulting asci were anatomized using a micromanipulator to obtain respective haploid cells (tetrad) and the auxotrophy was examined for each of the haploid cells. All of the thus obtained haploid cells were confirmed to have lysine synthesis capacity. The thus obtained NBRC10505(LYS2) strain and the NBRC10506 strain were mated and the resulting asci were anatomized using a micromanipulator to obtain the SW092-2D strain (genotype: MATa ura3 leu2 trp1 his3 ade2 LYS2).

The SW092-2D strain was transformed with the above-described DNA construct for homologous recombination and cultured in a tryptophan-free medium to select transformed yeasts. The transformed yeasts obtained in this manner are hereinafter referred to as "SW092-2D (Δpdc1::Lp.D-LDH1-TRP1) strain" and "SW092-2D (Δpdc1::Lp.D-LDH2-TRP 1) strain".

Example 6

D-lactic Acid Productivity Test 2

Using the SW092-2D (Δpdc1::Lp.D-LDH1-TRP1) strain, SW092-2D (Δpdc1::Lp.D-LDH2-TRP1) strain and a mini jar fermentor (manufactured by B.E. Marubishi Co., Ltd., 5 L), their fermentation was evaluated.

The SC3 medium shown in Table 1 was added to a test tube in an amount of 10 mL and a small amount of each strain was inoculated thereto and cultured overnight at 30° C. (pre-preculture). Then, to 45 mL of SC3 medium placed in an Erlenmeyer flask, 5 mL of the thus obtained pre-preculture medium was added and cultured at 30° C. for another 8 hours (preculture). The entire amount of the thus obtained preculture medium was inoculated to 1 L of SC3 medium placed in the mini jar fermentor and cultured for 30 hours. The culturing conditions are shown below:

pH: pH5
Aeration: 100 mL/min
Stirring: 120 rpm
Neutralizer: 1N sodium hydroxide.

The amount of the culture medium at the end of the culture period and the D-lactic acid and glucose concentrations in the culture medium were measured by "Glucose Test Wako C" (registered trademark) (manufactured by Wako Pure Chemical Industries, Ltd.) to determine the lactic acid yield with respect to saccharide based on the added glucose calculated from the thus measured lactic acid and glucose concentrations. As a result, it was confirmed that the SW092-2D (Δpdc1::Lp.D-LDH1-TRP1) and SW092-2D (Δpdc1::Lp.D-LDH2-TRP1) produced D-lactic acid with a lactic acid yield with respect to saccharide of 45% and 42%, respectively.

Comparative Example 1

Cloning of the D-LDH Gene Originated from Lactic Acid Bacterium and Evaluation of Fermentation As a D-LDH gene capable of efficiently performing fermentative production of D-lactic acid in transformed yeast, the D-LDH gene originated from the *Leuconostoc mesenteroides* ATCC 9135 strain is known (see WO 2004/104202). By cloning this D-LDH gene (hereinafter, referred to as "Lm. D-LDH gene") and introducing it into yeast to allow fermentation, the D-LDH activity of the Lm. D-LDH gene was examined by comparing it to that of the Lp. D-LDH1 gene or Lp. D-LDH2 gene originated from *Limulus polyphemus*.

Using a primer set (SEQ ID NOs:31 and 32) which was designed by referring to the nucleotide sequences described in WO 2004/104202 and the ATCC 9135 strain as template, the Lm. D-LDH gene was cloned by colony PCR (using "KOD-Plus-polymerase" manufactured by Toyobo Co., Ltd.). After purifying the thus obtained PCR-amplified fragment and phosphorylating the end thereof with "T4 Polynucleotide Kinase" (manufactured by Takara Bio Inc.), the fragment was ligated to the pUC118 vector (which had been digested with a restriction enzyme HincII and the cut surface had been dephosphorylated). The ligation was carried out using "DNA Ligation Kit Ver. 2" (manufactured by Takara Bio Inc.). *Escherichia coli* DH5α was transformed with the ligation plasmid product and the plasmid DNA was collected to obtain a plasmid into which the Lm. D-LDH gene was subcloned. The thus obtained pUC118 plasmid into which the Lm. D-LDH gene was inserted was digested with restriction enzymes XhoI and NotI, and the resulting DNA fragments were each inserted to the XhoI/NotI cleavage site of the vector pTRS11 for yeast expression. In this manner, Lm. D-LDH gene-expressing plasmid pTRS207 was obtained.

Next, the Lm. D-LDH gene was introduced into the PDC1 gene locus on the chromosome of the *Saccharomyces cerevisiae* SW092-2D strain in the same manner as in Example 5, except that the pTRS207 was used as template and the primer set shown in SEQ ID NO:33 was used in place of the primer shown in SEQ ID NO:24 or 26. The thus prepared transformed yeast is hereinafter referred to as "SW092-2D (Δpdc1::Lm. D-LDH-TRP1)". Then, in the same manner as in Example 6, the D-lactate productivity was evaluated by batch culture. As a result, the yield with respect to saccharide by the SW092-2D (Δpdc1::Lm. D-LDH-TRP1) was 38%. The result is shown in Table 2 along with the results of Example 6.

TABLE 2

| | Strain name | | |
|---|---|---|---|
| | SW092-2D (Δpdc1::Lp. D-LDH1-TRP1) | SW092-2D (Δpdc1::Lp. D-LDH2-TRP1) | SW092-2D (Δpdc1::Lm. D-LDH-TRP1) |
| Lactic acid yield with respect to saccharide (%) | 45 | 42 | 38 |

Reference Example 1

Preparation of a Yeast Introduced with the L-LDH Gene Originated from *Xenopus laevis*

In accordance with the method described in JP 2008-029329A, yeast in which the L-LDH gene originated from *Xenopus laevis* (X. L-LDH gene) was introduced into the PDC1 gene locus was prepared. As the yeast used for the introduction of the gene into the chromosome, a NBRC10506 strain in which the adenine auxotrophy is reverted (SU013-1D strain) was used. The SU013-1D strain was prepared by the following method. Using the plasmid pRS422 as template and the oligonucleotides (SEQ ID NOs:34 and 35) as primer set, PCR was performed to amplify a PCR fragment of about 2 kb corresponding to the ADE2 gene. After separating the PCR fragment by 1% agarose gel electrophoresis and purifying it in accordance with a conventional method, the PCR fragment was transformed to cancel the mutation in the ADE2 gene. By culturing the yeast strain in an adenine-free medium, a transformant in which the adenine synthesis capacity was reverted was selected.

To confirm that the thus obtained transformant is a yeast in which the mutation in the ADE2 gene was canceled, the following steps were carried out. First, diploid cells were obtained by mating the thus obtained transformant with the *Saccharomyces cerevisiae* LOGY77 strain having the wild-type ADE2 gene and the diploid cells were cultured in an ascus formation medium to allow ascus formation. The resulting asci were anatomized using a micromanipulator to obtain respective haploid cells (tetrad) and the auxotrophy was examined for each of the haploid cells. All of the thus obtained haploid cells were confirmed to have adenine synthesis capacity. The thus obtained NBRC10506(ADE2) strain and the NBRC10505 strain were mated and the resulting asci were anatomized using a micromanipulator to obtain the SU013-1D strain (genotype: MATα ura3 leu2 trp1 his3 ADE2 lys2). The thus obtained transformed yeast is hereinafter referred to as "SU013-1D (Δpdc1::X. L-LDH-TRP1) strain".

Example 7, Comparative Example 2

D-lactic Acid Productivity Test 3

The SU013-1D (Δpdc1::X. L-LDH-TRP1) strain prepared in Reference Example 1 was mated with each of the SW092-2D (Δpdc1::Lp. D-LDH1-TRP1) strain, SW092-2D (Δpdc1::Lp. D-LDH2-TRP1) strain and SW092-2D (Δpdc1::Lm. D-LDH-TRP1) strain, which were prepared in Example 5 and Comparative Example 1, thereby preparing diploid yeasts having the L-LDH gene and D-LDH gene heterozygously at the PDC1 gene locus. The thus prepared diploid yeasts are hereinafter referred to as "Lp1-X strain, Lp2-X strain and Lm-X strain, respectively".

Then, the Lp1-X strain, Lp2-X strain and Lm-X strain were batch-cultured under the same conditions as in Example 5, and the optical purity of the produced lactic acid was evaluated (Table 3).

TABLE 3

| | Strain name | | |
|---|---|---|---|
| | Lp1-X | Lp2-X | Lm-X |
| Yield of D-lactic acid (%) | 48.3 | 47.5 | 43.8 |
| Optical purity of D-lactic acid (%) | 52.3 | 51.7 | 44.4 |

As a result, the yeast having the D-LDH gene originated from *Limulus polyphemus* produced D-lactic acid with an optical purity of not less than 50%, while the optical purity of the D-lactic acid produced by the yeast having the D-LDH gene originated from *Leuconostoc mesenteroides* was 44.4%. Since the yield with respect to saccharide at which each yeast produces D-lactic acid and the optical purity of thereof are thought to be proportional to the D-LDH activity in the yeasts transformed with the D-LDH gene, from the results shown in Tables 2 and 3, it was confirmed that, when introduced into yeast, the D-LDH gene originated from *Limulus polyphemus* encodes a polypeptide having an activity higher than that of a polypeptide encoded by the D-LDH gene originated from *Leuconostoc mesenteroides*.

Example 8

Introduction of Multiple Copies of the D-LDH Gene into the Yeast Chromosome and Preparation of Temperature-Sensitive Mutant-Type PDC5 Yeast Next, preparation of a yeast introduced with the D-LDH gene originated from *Limulus polyphemus* also at gene loci other than the PDC1 gene locus was examined for the purpose of further improving the yield of D-lactic acid, and the D-LDH gene was introduced into the TDH3 gene whose introduction effect is described in JP 2008-029329A and the SED1 gene locus whose introduction effect is described in the international application PCT/JP2008/072129. Further, the temperature-sensitive mutant-type PDC5 gene described in JP 2008-048726A was also introduced.

[Introduction of the D-LDH Gene into the TDH3 Gene Locus]

For introduction into the TDH3 gene locus, in the same manner as the preparation method of the pTRS150 described in JP 2008-029329A, a plasmid pTRS208 in which the TDH3 terminator of the pTRS205 carrying the Lp. D-LDH1 gene was substituted with the ADH1 terminator was prepared. Then, using the SEQ ID NO:36 in place of the SEQ ID NO:8 of JP 2008-029329A as primer and the pTRS208 as template, a DNA construct for homologous recombination to be used for introduction into the TDH3 gene locus was obtained.

As the yeast into which the above-described DNA construct for homologous recombination is introduced, a leucine prototrophic strain of the SU013-1D strain (SW087-2C strain) was employed. The method of preparing the SW087-

2C strain is described in the followings. Using the plasmid pRS425 as template and the oligonucleotides (SEQ ID NOs: 37 and 38) as primer set, PCR was performed to amplify a PCR fragment of about 2 kb corresponding to the LEU2 gene. After separating the PCR fragment by 1% agarose gel electrophoresis and purifying it in accordance with a conventional method, the thus purified PCR fragment was transformed into the SU013-1D strain to cancel the mutation in the LEU2 gene. By culturing the yeast strain in a leucine-free medium, a transformant in which the leucine synthesis capacity was reverted was selected. To confirm that the thus obtained transformant is a yeast in which the mutation in the LEU2 gene was canceled, the following steps were carried out. First, diploid cells were obtained by mating the thus obtained transformant with the *Saccharomyces cerevisiae* LOGY77 strain having the wild-type LEU2 gene and the diploid cells were cultured in an ascus formation medium to allow ascus formation. The resulting asci were anatomized using a micromanipulator to obtain respective haploid cells (tetrad) and the auxotrophy was examined for each of the haploid cells. All of the thus obtained haploid cells were confirmed to have leucine synthesis capacity. The thus obtained SU013-1D(LEU2) strain and the NBRC10505 strain were mated and the resulting asci were anatomized using a micromanipulator to obtain the SW087-2C strain (genotype: MATα ura3 LEU2 trp1 his3 ADE2 lys2).

The SW087-2C strain was transformed with the above-described DNA construct for homologous recombination and cultured in a uracil-free medium for selection to obtain a transformed yeast introduced with the Lp. D-LDH1 gene at the TDH3 gene locus. The thus obtained transformed yeast is hereinafter referred to as "SW087-2C (ΔTDH3::Lp. D-LDH-URA3) strain".

[Introduction of the D-LDH Gene into SED1 Gene Locus]

The introduction into the SED1 gene locus was carried out by modifying the method described in Example 2 of the international application PCT/JP 008/072129. That is, using the pTRS205 in place of the pTRS102 as PCR template and the SEQ ID NO:39 in place of the SEQ ID NO:14 of the above-described international application publication as primer, a DNA construct for homologous recombination to be used for introduction into the SED1 gene locus was obtained.

As the yeast into which the above-described DNA construct for homologous recombination is introduced, SW092-7D strain (genotype: MATa ura3 leu2 trp1 his3 ADE2 LYS2), which was obtained by mating the NBRC10505(LYS2) strain prepared in Example 5 with the NBRC10506(ADE2) strain prepared in Reference Example 1 and separating by anatomization of the resulting asci with a micromanipulator, was employed.

The SW092-7D strain was transformed with the above-described DNA construct for homologous recombination and cultured in a histidine-free medium for selection to obtain a transformed yeast introduced with the Lp. D-LDH1 gene at the SED1 gene locus. The thus obtained transformed yeast is hereinafter referred to as "SW092-7D (ΔSED1::Lp. D-LDH-HIS3) strain".

[Introduction of the Temperature-Sensitive Mutant-Type PDC5 Gene (pdc5ts-9)]

As the yeast introduced with the temperature-sensitive mutant-type PDC5 gene, the yeast SW015 strain having the temperature-sensitive mutant-type PDC5 gene (pdc5ts-9), which is described in JP 2008-048726A, was employed. By mating the SW015 strain with the SW087-2C strain and separating by anatomization of the resulting asci with a micromanipulator, SW095-4B strain (genotype: MATα ura3 LEU2 trp1 his3 ADE2 lys2 pdc5ts-9 Δpdc1::TRP1) was obtained.

Further, by mating the SW095-4B strain with the SW092-2D strain and separating by anatomization of the resulting asci with a micromanipulator, SW098-21B strain (genotype: MATα ura3 LEU2 trp1 his3 ADE2 LYS2 pdc5ts-9) was obtained.

[Introduction of the D-LDH Gene into the PDC1, TDH3 and SED1 Gene Loci and Introduction of the Temperature-Sensitive Mutant-Type PDC5 Gene (pdc5ts-9)]

By using the thus prepared SW092-2D (ΔPDC1::Lp. D-LDH1-TRP1) strain, SW087-2C (ΔTDH3::Lp. D-LDH1-URA3) strain, SW092-7D (ΔTDH3::Lp. D-LDH1-HIS3) and SW098-21B, diploid mating and tetrad production were repeated to obtain SU042 strain which contains the Lp. D-LDH1 gene at the PDC1, TDH3 and SED1 gene loci and the temperature-sensitive mutant-type PDC5 (pdc5ts-9), the SU042 strain being diploid and not auxotrophic for adenine, leucine and lysine. The procedures for preparing the SU042 strain are shown in FIG. 1.

Example 9

D-lactic Acid Production Test 4

Using the SU042 strain prepared as described in Example 8, the D-lactic acid productivity was tested by batch culture. As the medium, the SC3 medium shown in Table 1 or a raw sugar medium (100 g/L "Yutosei" (manufactured by Muso Co., Ltd.), 1.5 g/L ammonium sulfate) was employed. First, the SU042 strain was cultured overnight with shaking in 5 ml of SC3 medium or raw sugar medium in a test tube (preculture). In a 500 ml Sakaguchi flask, the resulting preculture medium was inoculated to 50 ml of fresh SC3 medium or raw sugar medium and cultured for 24 hours with shaking (preculture). To a mini jar fermentor (manufactured by Able Co., Ltd., 2 L), 1 L of SC3 medium or raw sugar medium was added, and the temperature was adjusted (32° C.) and pH was controlled (pH 5, 5N calcium hydroxide). Culturing was carried out with aeration and stirring (at 200 mL/min and 400 rpm, respectively). As a result, the culture in the SC3 medium was finished in 30 hours and the yield with respect to saccharide was 63%. Further, the culture in the raw sugar medium was finished in 50 hours and the yield with respect to saccharide was 70%. From these results, it was confirmed that the performance of D-lactic acid fermentation was improved by the introduction of the Lp. D-LDH1 gene into the PDC1, TDH3 and SED1 gene loci and the introduction of the temperature-sensitive mutation into the PDC5 gene.

Example 10

D-lactic Acid Productivity Test by Continuous Culture

A continuous culture of the SU042 strain using the separation membrane described in WO 2007/097260 was examined. As the medium, a raw sugar medium (75 g/L "Yutosei" (manufactured by Muso Co., Ltd.), 1.5 g/L ammonium sulfate) was employed.

The culturing conditions are shown below:
Fermentation vessel capacity: 2 (L)
Culture medium volume: 1.5 (L)
Separation membrane used: PVDF membrane filter (described in Reference Example 2 of WO 2007/097260)
Effective filtration area of the membrane separation element: 120 cm$^2$
Temperature adjustment: 32 (° C.)

Aeration volume in the fermentation reaction vessel: air 0.02 (L/min), nitrogen gas 0.18 (L/min)

Stirring rate in the fermentation reaction vessel: 800 (rpm)

pH adjustment: adjusted to pH 5 with 5N calcium hydroxide

Sterilization: the culture vessel including the separation membrane element and medium used were all autoclaved at 121° C. for 20 minutes.

Figure 2:
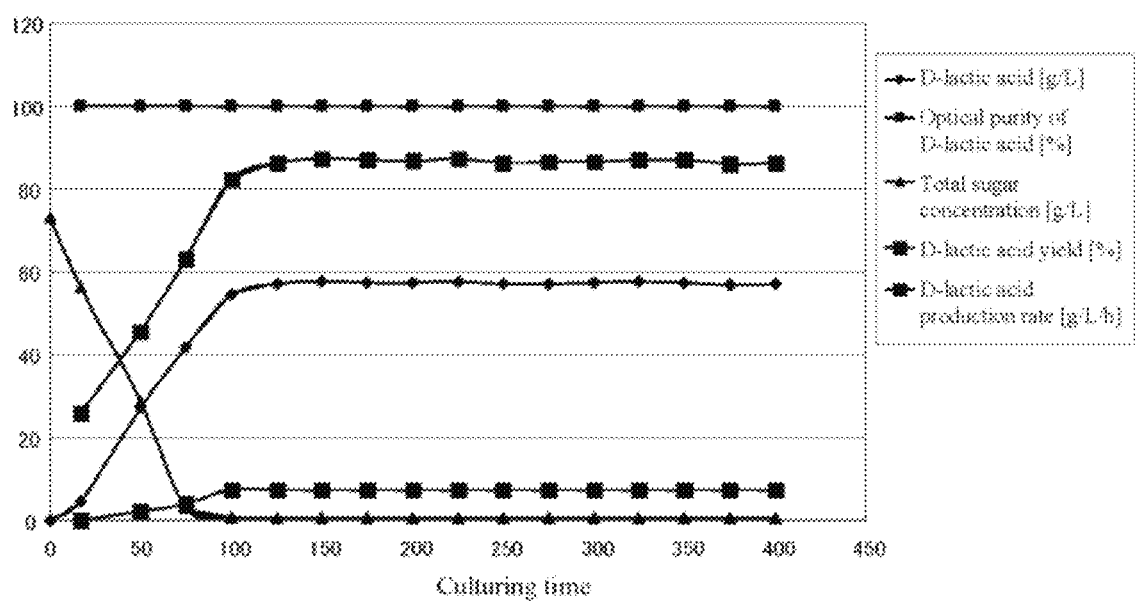
FIG. 2 shows the results of membrane-integrated continuous culture of yeast SU042 strain.

First, the SU042 strain was cultured at 30° C. overnight with shaking in 10 ml of the raw sugar medium in a test tube (pre-pre-preculture). The entire amount of the thus obtained culture medium was inoculated to 100 ml of fresh raw sugar medium and cultured in a 500 ml Sakaguchi flask for 24 hours at 30° C. with shaking (pre-preculture). The resulting pre-preculture medium was inoculated to 1.5 L of the raw sugar medium loaded in a membrane integrated-type continuous culture vessel (the apparatus shown in FIG. 2 of WO 2007/097260). Removal of the culture medium by a peristaltic pump (200 mL/h) was started 50 hours after the initiation of the culture, and the culture was continued until 400 hours to measure the concentration of lactic acid, which is the substance produced, and the lactic acid production rate. The results are shown in FIG. 2. It is noted here that the lactic acid production rate during the continuous culture was calculated using the Equation 1 below.

Lactic acid production rate (g/L·h)=product concentration in removed liquid (g/L)×removal rate of fermentation culture medium (L/hr)÷operational liquid volume of apparatus (L)  (Equation 1)

As a result of the continuous culture using the separation membrane, it was confirmed that the D-lactic acid yield with respect to saccharide was further improved to about 85% and that the D-lactic acid production rate was improved to 7.5 g/L·h.

Example 11

Introduction of the *Limulus polyphemus* D-LDH into *Candida utilis*

Next, using *Candida utilis*, which is a Crabtree-negative yeast, D-lactic acid was examined.

(a) Preparation of a vector for introduction of the *Limulus polyphemus* D-LDH gene First, a vector was constructed for introducing the D-LDH gene originated from *Limulus polyphemus* into the PDC1 gene locus on the *Candida utilis* chromosome. The *Candida utilis* NBRC0988 strain (hereinafter, referred to as "NBRC0988") was inoculated to YPD medium (1% Bacto Yeast Extract, 2% Bacto-peptone, 2% glucose) and cultured overnight at 30° C. From the thus obtained yeast cells, genomic DNA was extracted in accordance with a conventional method and used as template in the subsequent PCR. First, using the oligo DNAs shown in SEQ ID NOs:40 and 41 as primer set, a fragment containing the terminator region of the PDC1 gene was amplified. It is noted here that, unless otherwise specified, KOD-plus- (manufactured by Toyobo Co., Ltd.) was used as DNA polymerase in accordance with the attached protocol. After digesting the thus obtained fragment of about 1 kb with a restriction enzyme BssHI and purifying it, the resultant was ligated to pBluescriptIISK(+) which had been previously digested with restriction enzyme BssHI in the same manner. The thus obtained plasmid is hereinafter referred to as "pKS01".

Next, in the same manner, using the genomic DNA of NBRC0988 as template and the oligo DNAs shown in SEQ ID NOs:42 and 43 as primer set, PCR was performed to amplify a fragment containing the PGK promoter. The thus obtained fragment of about 1 kb was purified and used in the subsequent experiments. Then, using the plasmid pLC1-hph having the hph gene capable of imparting resistance against hygromycin B which is a type of antibiotic substance as template and the oligo DNAs shown in SEQ ID NOs:44 and 45 as primer set, PCR was performed to amplify a fragment containing the hph gene, which was then purified to obtain a fragment of about 1.1 kb. Further, using the genomic DNA of NBRC0988 as template and the oligo DNAs shown in SEQ ID NOs:46 and 47 as primer set, PCR was performed to amplify a fragment containing the GAP terminator, which was then purified to obtain a fragment of about 500 bp.

The fragment containing the PGK promoter, the fragment containing the hph gene and the fragment containing the GAP terminator that were obtained in the above-described manner were mixed, and using the oligo DNAs shown in SEQ ID NOs:48 and 49 as primer set, PCR was performed to amplify a fragment in which the PGK promoter, hph gene and GAP terminator were linked. After phosphorylating the end of the thus obtained fragment of about 2.6 kb, the fragment was ligated to the pUC118 which had been digested with HincII and dephosphorylated. The thus obtained plasmid is hereinafter referred to as "pKS02".

Next, in the same manner, using the genomic DNA of NBRC0988 as template and the oligo DNAs shown in SEQ ID NOs:50 and 51 as primer set, PCR was performed to amplify a fragment containing the PGK terminator, which was then purified to obtain a fragment of about 500 bp. Further, using the pKS02 obtained in the above-described manner as template and the oligo DNAs shown in SEQ ID NOs:52 and 53 as primer set, PCR was performed to amplify a fragment in which the PGK promoter, hph gene and GAP terminator were linked, which was then purified to obtain a fragment of about 2.6 kb.

The fragment containing the PGK terminator and the fragment in which the PGK promoter, hph gene and GAP terminator were linked, which fragments were obtained in the above-described manner, were mixed, and using the oligo DNAs shown in SEQ ID NOs:50 and 53 as primer set, PCR was performed to amplify a fragment in which the PGK terminator, PGK promoter, hph gene and GAP terminator were linked. After digesting the thus obtained fragment of about 3 kb with restriction enzymes BamHI and ClaI and purifying it, the resultant was ligated to the pKS02 which had been previously digested with restriction enzymes BamHI and ClaI in the same manner. The thus obtained plasmid is hereinafter referred to as "pKS03".

Next, in the same manner, using the genomic DNA of NBRC0988 as template and the oligo DNAs shown in SEQ ID NOs:54 and 55 as primer set, PCR was performed to amplify a fragment containing the PDC1 promoter region, which was then purified to obtain a fragment of about 2.1 kb. Further, using the pTRS205 prepared in Example 2 as template and the oligo DNAs shown in SEQ ID NOs:56 and 57 as primer set, PCR was performed to amplify a fragment containing the D-LDH gene originated from *Limulus polyphemus*, which was then purified to obtain a fragment of about 1 kb.

The fragment containing the PDC1 promoter region and the fragment containing the D-LDH gene originated from *Limulus polyphemus* that were obtained in the above-described manner were mixed, and using the oligo DNAs shown in SEQ ID NOs:54 and 57 as primer set, PCR was performed to amplify a fragment in which the fragment containing the PDC1 promoter region and the fragment containing the D-LDH gene originated from *Limulus polyphemus* were linked. After digesting the thus obtained fragment of about 3.1 kb with restriction enzymes NotI and BglII and purifying it, the resultant was ligated to the pKS03 which had been previously digested with restriction enzymes NotI and BamHI in the same manner. The thus obtained plasmid is hereinafter referred to as "pKS04".

(b) Introduction of the *Limulus polyphemus* D-LDH Gene into the PDC1 Gene Locus The pKS04 obtained in the above-described manner was digested with restriction enzyme BglII and introduced into NBRC0988 by the electroporation method. A small amount of the cells was inoculated to YPD medium and cultured overnight at 30° C. After centrifuging the culture to discard the supernatant, the cells were washed with sterilized water and 1M sorbitol and eventually suspended in 1M sorbitol. Then, after mixing the cells and the pKS04 digested with restriction enzyme BglII and leaving the resulting mixture on ice for 5 minutes, the mixture was transferred to an electroporation cuvette and subjected to electroporation at a capacitance of 25 µF, voltage of 0.75 kV and resistance of 800Ω. Thereafter, the mixture was transferred to YPD medium containing 1M sorbitol and cultured at 30° C. for about 4 hours, and then applied to YPD medium supplemented with 600 µg/L of hygromycin B. From the resulting hygromycin B-resistant strain, the genome thereof was extracted, and by verifying that fragments of about 3 kb and 2 kb were each amplified by PCR using the oligo DNAs shown in SEQ ID NOs:54 and 57 and SEQ ID NOs:56 and 51 as respective primer sets, it was confirmed that a transformed yeast in which the D-LDH gene originated from *Limulus polyphemus* was introduced into the PDC1 gene locus was obtained. The thus obtained transformed yeast is hereinafter referred to as "CuLpLDH strain".

Comparative Example 2

Introduction of D-LDH Originated from Lactic Acid Bacterium into *Candida utilis*

In the same manner as in Example 11, the D-LDH gene originated from a lactic acid bacterium, *Leuconostoc mesenteroides*, was introduced. It is noted, however, that the oligo DNA shown in SEQ ID NO:58 was employed in place of the one shown in SEQ ID NO:55 used in Example 11. In addition, the pTRS207 obtained in Comparative Example 1 was used as template in place of the pTRS205 obtained in Example 2 and the oligo DNAs shown in SEQ ID NOs:59 and 60 were used in place of those shown in SEQ ID NOs:56 and 57. The thus obtained plasmid is hereinafter referred to as "pKS05".

The plasmid obtained in the above-described manner was introduced into the NBRC0988 strain in the same manner as in Example 11. The thus obtained strain in which the D-LDH gene originated from a lactic acid bacterium, *Leuconostoc mesenteroides*, was introduced into the PDC1 gene locus is hereinafter referred to as "CuLmLDH strain".

Example 12, Comparative Example 3

D-lactic Productivity Test in *Candida utilis*

Using the CuLpLDH strain and the CuLmLDH strain prepared in Example 11 and Comparative Example 2, respectively, their D-lactic acid productivity was evaluated. YPD medium was added in an amount of 50 ml to a 500 ml Sakaguchi flask, and the CuLpLDH and CuLmLDH strains were inoculated thereto in small amounts and cultured at 30° C. overnight with shaking (preculture). After collecting the culture medium and washing it with fresh YPD medium, the culture medium was placed and cultured in a mini-jar fermentor in which 1 L of YPD10 medium (containing 10% glucose) was added. The culturing conditions are shown below:
Amount of initial inoculation: inoculated at $OD_{600}$=10
pH: pH6
Aeration: 100 mL/min
Stirring: 120 rpm
Neutralizer: 1N calcium hydroxide
Culturing temperature: 35° C.

The culture was carried out for 40 hours and the lactic acid concentration and glucose concentration of the culture medium at 40 hours were analyzed. Glucose had been completely consumed. In addition, as shown in Table 4, from the analysis results of the productivity per glucose consumption (yield with respect to saccharide) and the optical purity of D-lactic acid, the yeast (*Candida utilis*) introduced with the D-LDH gene was found to be capable of fermentatively producing D-lactic acid and the CuLpLDH strain introduced with the D-LDH gene originated from *Limulus polyphemus* had a higher yield.

Example 13, Comparative Example 4

D-lactic Productivity Test 2 in *Candida utilis*

Next, using the CuLpLDH and CuLmLDH strains, their D-lactic acid productivity using xylose, which is a pentose, as sugar source was evaluated. YPD medium was added in an amount of 50 ml to a 500 ml Sakaguchi flask, and the CuLpLDH and CuLmLDH strains were inoculated thereto in small amounts and cultured at 30° C. overnight with shaking (preculture). After collecting the culture medium and washing it with fresh YPD medium, the culture medium was placed and cultured in a mini jar fermentor in which 1 L of YPX10 medium (1% yeast extract, 2% Bacto-peptone, 4% xylose) was added. The culturing conditions are shown below:
Amount of initial inoculation: inoculated at $OD_{600}$=10
pH: pH6
Aeration: 100 mL/min
Stirring: 120 rpm
Neutralizer: 1N calcium hydroxide
Culturing temperature: 30° C.

The culture was carried out for 60 hours and the lactic acid concentration and xylose concentration of the culture medium at 60 hours were analyzed. Xylose had been completely consumed. In addition, as shown in Table 4, from the analysis results of the productivity per xylose consumption (yield with respect to saccharide) and the optical purity of D-lactic acid, the yeast (*Candida utilis*) introduced with the D-LDH gene was found to be capable of fermentatively producing D-lactic acid using xylose as starting material and the CuLpLDH strain introduced with the D-LDH gene originated from *Limulus polyphemus* had a higher yield.

TABLE 4

|  | Example 12 | Example 13 | Comparative Example 3 | Comparative Example 4 |
|---|---|---|---|---|
| Strain name | CuLpLDH | CuLpLDH | CuLmLDH | CuLmLDH |
| Sugar source | glucose | xylose | glucose | xylose |
| D-lactic acid yield with respect to saccharide (%) | 29 | 23 | 22 | 17 |
| Optical purity of D-lactic acid (% e.e.) | 99.9 | 99.9 | 99.9 | 99.9 |

Industrial Applicability

We stably produce D-lactic acid at a low cost, and since the produced D-lactic acid has a high optical purity, it is preferably used as a raw material for polymers.

The invention claimed is:

1. A vector comprising an isolated polynucleotide comprising any one of the following (a) to (g):
   (a) a polynucleotide having the nucleotide sequence shown in SEQ ID NO:3 or 4;
   (b) a polynucleotide having the same nucleotide sequence as shown in SEQ ID NO:3 or 4 except that at least one and up to 40 nucleotides are substituted, deleted, inserted and/or added, which polynucleotide encodes a polypeptide having a D-lactate dehydrogenase (D-LDH) activity;
   (c) a polynucleotide which hybridizes under highly stringent conditions in the presence of 50% formamide at 65° C. with the polynucleotide having the nucleotide sequence shown in SEQ ID NO:3 or 4 or a full complementary strand thereof, which polynucleotide encodes a polypeptide having a D-LDH activity;
   (d) a polynucleotide having a nucleotide sequence which has a sequence identity of not less than 95% to the nucleotide sequence shown in SEQ ID NO:3 or 4, which polynucleotide encodes as polypeptide haying a D-lactate dehydrogenase activity;
   (e) a polynucleotide encoding as polypeptide having the amino acid sequence shown in SEQ ID NO: 1 or 2;
   (f) a polynucleotide encoding a polypeptide having an amino acid sequence which has a sequence identity of not less than 95% to the amino acid sequence shown in SEQ ID NO:1 or 2, which polypeptide has a D-lactate dehydrogenase activity; and
   (g) a polynucleotide encoding a polypeptide having the same amino acid sequence as shown in SEQ ID NO:1 or 2 except that at least one and up to 10 amino acids are substituted, deleted, inserted and/or added, which polypeptide has a D-lactate dehydrogenase activity.

2. A vector comprising a polynucleotide of any one of the following (a) to (g):
   (a) a polynucleotide having the nucleotide sequence shown in SEQ ID NO:3 or 4;
   (b) a polynucleotide having the same nucleotide sequence as shown in SEQ ID NO:3 or 4 except that at least one and up to 40 nucleotides are substituted, deleted, inserted and/or added, which polynucleotide encodes a polypeptide having a D-lactate dehydrogenase (D-LHD) activity;
   (c) a polynucleotide which hybridizes under highly stringent conditions in the presence of 50% formamide at 65° C. with the polynucleotide having the nucleotide sequence shown in SEQ ID NO:3 or 4 or a full complementary strand thereof, which polynucleotide encodes a polypeptide having a D-LDH activity;
   (d) a polynucleotide having a nucleotide sequence which has a sequence identity of not less than 95% to the nucleotide sequence shown in SEQ ID NO:3 or 4, which polynucleotide encodes a polypeptide having a D-lactate dehydrogenase activity;
   (e) a polynucleotide encoding a polypeptide having the amino acid sequence shown in SEQ ID NO:1 or 2;
   (f) a polynucleotide encoding a polypeptide having an amino acid sequence which has a sequence identity of not less than 95% to the amino acid sequence shown in SEQ ID NO:1 or 2, which polypeptide has a D-lactate dehydrogenase activity; and
   (g) a polynucleotide encoding a polypeptide having the same amino acid sequence as shown in SEQ ID NO:1 or 2 except that at least one and up to 10 amino acids are substituted, deleted, inserted and/or added, which polypeptide has a D-lactate dehydrogenase activity, and a promoter capable of expressing said polynucleotide are linked.

3. The vector according to claim 2, wherein the promoter is a promoter of pyruvate decarboxylase 1 gene (PDC1 gene), suppression-of-exponential-defect 1 gene (SED1 gene) or glyceraldehyde-3-phosphate dehydrogenase 3 gene (TDH3 gene).

4. The vector according to claim 2, wherein said promoter is selected from any one of the following (I) to (III):
   (I) a promoter having the nucleotide sequence shown in any one of SEQ ID NOs:5 to 7;
   (II) a promoter having a nucleotide sequence which hybridizes under highly stringent conditions in the presence of 50% formamide at 65° C. with the nucleotide sequence shown in any one of SEQ ID NOs:5 to 7; and
   (III) a promoter having the same nucleotide sequence as shown in any one of SEQ ID NOs:5 to 7 except that one or several nucleotides are deleted, substituted and/or added wherein the nucleotide sequence encodes a polypeptide having not less than 95% sequence identity within the polypeptide encoded by one of SEQ ID NOs:5 to 7.

5. A host cell transformed with a polynucleotide comprising any one of the following (a) to (g):
   (a) a polynucleotide having the nucleotide sequence shown in SEQ ID NO:3 or 4;
   (b) a polynucleotide having the same nucleotide sequence as shown in SEQ ID NO:3 or 4 except that at least one and up to 40 nucleotides are substituted, deleted, inserted and/or added, which polynueleotide encodes a polypeptide having a D-lactate dehydrogenase (D-LDH) activity;
   (c) a polynucleotide which hybridizes under highly stringent conditions in the presence of 50% formamide at 65° C. with the polynucleotide having the nucleotide sequence shown in SEQ ID NO:3 or 4 or a full complementary strand thereof, which polynucleotide encodes a polypeptide having a D-LDH activity;
   (d) a polynucleotide having a nucleotide sequence which has a sequence identity of not less than 95% to the nucleotide sequence shown in SEQ NO:3 or 4, which polynucleotide encodes a polypeptide having a D-lactate dehydrogenase activity;
   (e) a polynucleotide encoding a polypeptide having the amino acid sequence shown in SEQ ID NO:1 or 2;
   (f) a polynucleotide encoding a polypeptide having an amino acid sequence which has a sequence identity of not less than 95% to the amino acid sequence shown in SEQ ID NO:1 or 2, which polypeptide has a D-lactate dehydrogenase activity; and
   (g) a polynucleotide encoding a polypeptide having the same amino acid sequence as shown in SEQ ID NO:1 or 2 except that at least one and up to 10 amino acids are substituted, deleted, inserted and/or added, which polypeptide has a D-lactate dehydrogenase activity, is introduced.

6. A transformed yeast in which a polynucleotide comprising any one of the following (a) to (g):
   (a) a polynucleotide having the nucleotide sequence shown in SEQ ID NO:3 or 4;
   (b) a polynucleotide having the same nucleotide sequence as shown in SEQ ID NO:3 or 4 except that at least one and up to 40 nucleotides are substituted, deleted, inserted and/or added, which polynucleotide encodes a polypeptide having a D-lactate dehydrogenase (D-LDH) activity;

(c) a polynucleotide which hybridizes under highly stringent conditions in the presence of 50% formamide at 65° C. with the polynucleotide having the nucleotide sequence shown in SEQ ID NO:3 or 4 or a full complementary strand thereof, which polynucleotide encodes a polypeptide having a D-LDH activity;
(d) a polynucleotide having a nucleotide sequence which has a sequence identity of not less than 95% to the nucleotide sequence shown in SEQ NO:3 or 4, which polynucleotide encodes a polypeptide having D-lactate dehydrogenase activity;
(e) a polynucleotide encoding a polypeptide haying the amino acid sequence shown in SEQ ID NO:1 or 2;
(f) a polynucleotide encoding a polypeptide having an amino acid sequence which has a sequence identity of not less than 95% to the amino acid sequence shown in SEQ ID NO:1 or 2, which polypeptide has a D-lactate dehydrogenase activity; and
(g) a polynucleotide encoding a polypeptide having the same amino acid sequence as shown in SEQ ID NO:1 or 2 except that at least one and up to 10 amino acids are substituted, deleted, inserted and/or added, which polypeptide has a D-lactate dehydrogenase activity, is introduced.

7. The transformed yeast according to claim 6, wherein at least one of pyruvate decarboxylase 1 gene (PDC1 gene), suppression-of-exponential-defect 1 gene (SED1 gene) and glyceraldehyde-3-phosphate dehydrogenase 3 gene (TDH3 gene) of said transformed yeast is substituted with the polynucleotide.

8. The transformed yeast according to claim 7, wherein at least one of said genes is PDC1 gene.

9. A method of producing D-lactic acid, which comprises the step of culturing the host cell according to claim 5.

10. A transformant in which the vector of claim 2 is introduced.

11. A transformed yeast in which the vector of claim 2 is introduced.

12. The transformed yeast according to claim 6, wherein at least one of pyruvate decarboxylase 1 gene (PDC1 gene), suppression-of-exponential-defect 1 gene (SED1 gene) and glyceraldehyde-3-phosphate dehydrogenase 3 gene (TDH3 gene) of said transformed yeast is substituted with the DNA construct comprising the polynucleotide linked to a promoter capable of expressing the polynucleotide.

13. The transformed yeast according to claim 12, wherein at least one of said genes is PDC1 gene.

14. A method of producing D-lactic acid, which comprises the step of culturing the transformed yeast according to claim 6.

* * * * *